United States Patent
Emmanouilidou et al.

(10) Patent No.: US 9,848,848 B2
(45) Date of Patent: Dec. 26, 2017

(54) LUNG SOUND DENOISING STETHOSCOPE, ALGORITHM, AND RELATED METHODS

(71) Applicant: The Johns Hopkins University, Baltimore, MD (US)

(72) Inventors: Dimitra Emmanouilidou, Baltimore, MD (US); Mounya Elhilali, Silver Spring, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 0 days.

(21) Appl. No.: 14/755,954

(22) Filed: Jun. 30, 2015

(65) Prior Publication Data

US 2016/0015359 A1 Jan. 21, 2016

Related U.S. Application Data

(60) Provisional application No. 62/019,054, filed on Jun. 30, 2014.

(51) Int. Cl.
*A61B 7/04* (2006.01)
*A61B 7/00* (2006.01)
*A61B 7/02* (2006.01)

(52) U.S. Cl.
CPC .............. *A61B 7/003* (2013.01); *A61B 7/026* (2013.01); *A61B 7/04* (2013.01)

(58) Field of Classification Search
CPC ....... A61B 7/04; H04R 2410/05; H04R 3/005
(Continued)

(56) References Cited

U.S. PATENT DOCUMENTS 5,010,889 A * 4/1991 Bredesen ................. A61B 7/04
                                                                        381/67
5,812,678 A * 9/1998 Scalise ................... A61B 7/003
                                                                        381/67
(Continued)

OTHER PUBLICATIONS

Upadhyay, Navneet, and Abhijit Karmakar. "An Improved Multi-Band Spectral Subtraction Algorithm for Enhancing Speech in Various Noise Environments." Procedia Engineering, vol. 64, 2013, pp. 312-321.*

(Continued)

*Primary Examiner* — Joseph Saunders, Jr.
*Assistant Examiner* — James Mooney
(74) *Attorney, Agent, or Firm* — Venable LLP; Henry J. Daley

(57) ABSTRACT

An electronic stethoscope includes an acoustic sensor assembly having a first microphone to detect biological sounds within a body, a detection system in communication with the first microphone to receive an auscultation signal from the first microphone, the auscultation signal including information of the biological sounds detected by the first microphone. The stethoscope also includes a second microphone in communication with the detection system to detect noise from an environment of the body. The detection system receives a noise signal from the second microphone, and provides a resultant signal based on the auscultation signal and the noise signal. The detection system subtracts information from the auscultation signal to produce the resultant signal, where the subtracted information is based on the noise signal such that the subtracted information is based more on higher frequency ranges of the noise signal compared to a lower frequency range corresponding to the biological sounds.

21 Claims, 13 Drawing Sheets

(58) Field of Classification Search
USPC .................. 381/67, 56, 91, 71.1, 94.1, 94.7
See application file for complete search history.

(56) References Cited

U.S. PATENT DOCUMENTS

| | | | | |
|---|---|---|---|---|
| 2004/0037429 | A1* | 2/2004 | Candioty | A61B 7/04 381/67 |
| 2011/0213271 | A1* | 9/2011 | Telfort | A61B 7/003 600/586 |
| 2014/0288452 | A1* | 9/2014 | Mittal | A61B 7/04 600/513 |

OTHER PUBLICATIONS

Kamath, Sunil D., and Philipos C. Loizou. "A Mult-Band Spectral Subtraction Method for Enhancing Speech Corrupted by Colored Noise." IEEE, 2002.*

Al-Naggar, "A new method of lung sounds filtering using modulated least mean square-adaptive noise cancellation," J. Biomed. Sci. Eng., vol. 2013, pp. 869-876, Sep. 2013.

Bahoura et al., "Respiratory sounds denoising using wavelet packets," in Proc. 2nd Int. Conf. Bioelectromagn., 1998, pp. 11-12.

Beh et al., "Spectral subtraction using spectral harmonics for robust speech recognition in car environments," in Proc. Int. Conf. Comput. Sci., 2003, pp. 1109-1116.

Berouti et al., "Enhancement of speech corrupted by acoustic noise," in Proc. IEEE Int. Conf. Acoust., Speech, Signal Process., Apr. 1979, vol. 4, pp. 208-211.

Boll, "Suppression of acoustic noise in speech using spectral subtraction," IEEE Trans. Acoust, Speech, Signal Process., vol. ASSP-27, No. 2, pp. 113-120, Apr. 1979.

Chang et al., "Performance evaluation and enhancement of lung sound recognition system in two real noisy environments," Comput. Methods Progr. Biomed, vol. 97, No. 2, pp. 141-150, 2010.

Chowdhury et al.,"Frequency analysis of adventitious lung sounds," Journal of biomedical engineering, vol. 4, No. 4, pp. 305-312, Oct. 1982.

Ellington et al., "Developing a reference of normal lung sounds in healthy peruvian children," Lung, vol. 192, pp. 765-773, Jun. 19, 2014.

Emmanouilidou et al., "A multiresolution analysis for detection of abnormal lung sounds," in Proc. IEEE Annu. Int. Conf. Eng. Med. Biol. Soc., 2012, pp. 3139-3142.

Emmanouilidou et al., "Characterization of noise contaminations in lung sound recordings," in Proc. IEEE 35th Annu. Int. Conf. Eng. Med. Biol. Soc., 2013, pp. 2551-2554.

Flietstra et al.,"Automated analysis of crackles in patients with interstitial pulmonary fibrosis," Pulmonary Med., vol. 2011, No. 2, pp. 5905-5906, 2011.

Gavriely et al., "Spectral characteristics of chest wall breath sounds in normal subjects," Thorax, vol. 50, No. 12, pp. 1292-1300, Dec. 1995.

Ghaderi et al., "Localizing heart sounds in respiratory signals using singular spectrum analysis," Biomed. Eng., vol. 58, No. 12, pp. 3360-3367, Dec. 2011.

Guntupalli et al., "Validation of automatic wheeze detection in patients with obstructed airways and in healthy subjects," J. Asthma, Off. J. Assoc. Care Asthma, vol. 45, No. 10, pp. 903-907, Dec. 2008.

Gurung et al., "Computerized lung sound analysis as diagnostic aid for the detection of abnormal lung sounds: A systematic review and meta-analysis," Respir. Med, vol. 105, No. 9, pp. 1396-1403, Sep. 2011.

Hadjileontiadis, "Empirmical mode decomposition and fractal dimension filter: a novel technique for denoising explosive lung sounds," IEEE Eng. Med. Biol. Mag., vol. 26, No. 1, pp. 30-39, Jan. 2007.

Hadjileontiadis, Lung Sounds: An Advanced Signal Processing Perspective. San Rafael, CA, USA: Morgan & Claypool, 2009, vol. 3, No. 1.

Hossain et al., "An overview of heart-noise reduction of lung sound using wavelet transform based filter," in Proc. IEEE 25th Annu. Int. Conf. Eng. Med. Biol. Soc., 2003, vol. 1, pp. 458-461.

Kates et al., "Coherence and the speech intelligibility index," J. Acoust. Soc. Amer., vol. 117, No. 4, pp. 2224-2237, 2005.

Kuhn et al., "Stochastic modeling of the Nlms algorithm for complex gaussian input data and nonstationary environment," Digital Signal Process., vol. 30, pp. 55-66, 2014.

Kuo et al., "Active noise control: A tutorial review," Proc. IEEE, vol. 87, No. 6, pp. 943-973, Jun. 1999.

Lockwood et al., "Experiments with a nonlinear spectral subtractor (NSS), hidden Markov models and the projection, for robust speech recognition in cars," Speech Commun., vol. 11, Nos. 2/3, pp. 215-228, 1992.

Loizou, Speech Enhancement: Theory and Practice, 2nd ed. Boca Raton, FL, USA: CRC Press, 2013.

Lu and M. Bahoura, "An integrated automated system for crackles extraction and classification," Biomed. Signal Process. Control, vol. 3, No. 3, pp. 244-254, Jul. 2008.

Ma et al., "Objective measures for predicting speech intelligibility in noisy conditions based on new band-importance functions," J. Acoust. Soc. Amer., vol. 125, No. 5, pp. 3387-3405, May 2009.

Meslier et al.,"Wheezes," Eur. Respir. J.,vol. 8,No. 11, pp. 1942-1948, Nov. 1995.

Molaie et al., "A chaotic viewpoint on noise reduction from respiratory sounds," Biomed. Signal Proc. Control, vol. 10, pp. 245-249, 2014.

Nelson et al., "Noise control challenges for auscultation on medical evacuation helicopters," Appl. Acoust., vol. 80, pp. 68-78, 2014.

Pasterkamp et al., "Nomenclature used by health care professionals to describe breath sounds in asthma," Chest, vol. 92, No. 2, pp. 346-352, Aug. 1987.

Patel et al., "An adaptive noise reduction stethoscope for auscultation in high noise environments," J. Acoust. Soc. Amer., vol. 103, No. 5, pp. 2483-2491, May 1998.

Piirila et al., "Crackles: Recording, analysis and clinical significance," Eur. Respir. J., vol. 8, No. 12, pp. 2139-2148, Dec. 1995.

Prasad, "A review of different approaches of spectral subtraction algorithms for speech enhancement," Curr. Res. Eng., vol. 1, No. 2, pp. 57-64, 2013.

Reichert et al., "Analysis of respiratory sounds: State of the art," Clin. Med. Circulatory Respir. Pulmonary Med., vol. 2, pp. 45-58, 2008.

Riella et al., "Method for automatic detection of wheezing in lung sounds," Brazilian J. Med. Biol. Res., vol. 42, No. 7, pp. 674-684, Jul. 2009.

Singh et al., "Speech enhancement using critical band spectral subtraction," in Proc. Int. Conf. Spoken Lang. Proc. Sydney, Australia, 1979, pp. 2827-2830.

Sovijärvi et al., "Standardization of computerized respiratory sound analysis," Eur. Respir. Rev., vol. 10, No. 77, p. 585, 2000.

Suzuki et al., "Real-time adaptive cancelling of ambient noise in lung sound measurement," Med. Biol. Eng. Comput., vol. 33, No. 5, pp. 704-708, Sep. 1995.

Valin and I. B. Collings, "Interference-normalized least mean square algorithm," IEEE Signal Proc. Lett., vol. 14, No. 12, pp. 988-991, Dec. 2007.

Vary, "Noise suppression by spectral magnitude estimation-mechanism and theoretical limits," Signal Process., vol. 8, pp. 387-400, 1985.

* cited by examiner

LUNG SOUND DENOISING STETHOSCOPE, ALGORITHM, AND RELATED METHODS

CROSS-REFERENCE TO RELATED APPLICATIONS

This application claims priority to U.S. Provisional Application No. 62/019,054 filed Jun. 30, 2014, the entire contents of which are hereby incorporated by reference.

STATEMENT OF GOVERNMENT SUPPORT

This invention was made with Government support under IIS-0846112, awarded by the National Science Foundation; NIH 1R01AG036424, awarded by the National Institutes of Health; N00014-12-1-0740, awarded by the Office of Naval Research; and N000141010278, awarded by the Office of Naval Research. The Government has certain rights in this invention.

TECHNICAL FIELD

The field of the currently claimed embodiments of the invention relates to devices, systems, and methods for acoustic monitoring, particularly for acoustic monitoring of bodily functions preferentially over unwanted sounds and for differentiating among different sounds.

BACKGROUND

The use of chest auscultation to diagnose lung conditions, including infections, chronic conditions and other characteristics of the lungs, has been in practice since the invention of the stethoscope in the early 1800s. It is a diagnostic instrument widely used by clinicians to "listen" to lung sounds and flag abnormal patterns that emanate from pathological effects on the lungs. While the stethoscope can be complemented by other clinical tools—including chest radiography and other imaging techniques, or chest percussion and palpation—the stethoscope remains a key diagnosis device due to its low-cost and non-invasive nature. Chest auscultation with standard acoustic stethoscopes is not limited to resource-rich industrialized settings. In low-resource, high-mortality countries with relatively weak health care systems, there is limited access to diagnostic tools like chest radiographs or basic laboratories. As a result, health care providers with variable training and supervision rely upon low-cost clinical tools like standard acoustic stethoscopes to make critical patient management decisions. Indeed, their use is even more pervasive in resource poor areas where low-cost exams are of paramount importance, access to complimentary clinical tools is limited or nonexistent and health care personnel operate with minimal training. Despite its universal adoption, the use of the stethoscope is riddled by a number of issues including subjectivity in interpretation of chest sounds, inter-listener variability and inconsistency, need for advanced medical expertise, and vulnerability to ambient noise that can mask the presence of sound patterns of interest. Thus, while chest auscultation constitutes a portable low cost tool widely used for respiratory disease detection and offers a powerful means of pulmonary examination, it remains riddled with a number of issues that limit its diagnostic capability. Particularly, patient agitation (especially in children), background chatter, and other environmental noises often contaminate the auscultation, hence affecting the clarity of the lung sound itself.

Electronic auscultation combined with computerized lung sound analysis can be used to remedy some of the inconsistency limitations of stethoscopes and provide an objective and standardized interpretation of lung sounds. However, the success of electronic auscultations has been limited to well controlled or quiet clinical settings with adult subjects. The presence of background noise contaminations usually impedes the applicability of these algorithms or leads to unwanted false positives. Contamination of the lung signal picked up by the stethoscope with undesirable noise remains an unaddressed issue, limiting the deployment of computerized auscultation technologies and hampering the usefulness of the stethoscope tool itself, particularly in outpatient clinics or busy health centers where surrounding background noise is an inevitable and hard to control condition. The noise issue is further compounded in pediatric patients where child agitation and crying can add to the distortion of the lung signal picked up by the stethoscope microphone.

Since the invention of the stethoscope, chest auscultations offer a low-cost, highly portable, non-invasive and widely used tools for physical examination of pulmonary health and respiratory disease detection. While they can be complemented with other clinical tools (e.g., chest X-rays), stethoscopes are sometimes the only means of pulmonary examination in low-resource settings such as clinics or health centers in rural or impoverished communities. Such settings usually raise additional challenges for clinical diagnosis pertaining to the examination environment itself. For example, patient agitation (especially in children), background chatter, and other environmental noises can contaminate the sound signal picked up by the stethoscope, hence affecting the clarity of the lung sound itself. Such distortion affects the clarity of the lung sound, hence limiting its clinical value for the health care practitioner. It also impedes the use of electronic auscultation combined with computerized lung sound analysis. However, previous electronic or automated approaches have mainly been validated in well-controlled or quiet clinical settings with adult subjects. In real world settings, the presence of background noise impedes the applicability of pre-existing systems or leads to unwanted false positives. Accordingly, there exists a need to improve the quality of auscultation signals against background contaminations.

SUMMARY

An electronic stethoscope according to an embodiment of the current invention includes an acoustic sensor assembly having a first microphone arranged to detect biological sounds within a body under observation; a detection system in communication with the first microphone and configured to receive an auscultation signal from the first microphone, the auscultation signal including information of the biological sounds detected by the first microphone; and a second microphone arranged to detect noise from an environment of the body, the second microphone being in communication with the detection system, which is arranged to receive a noise signal from the second microphone. The detection system is configured to provide a resultant signal based on the auscultation signal and the noise signal, and to subtract information from the auscultation signal to produce the resultant signal. The subtracted information is based on the noise signal such that the subtracted information is based more on higher frequency ranges of the noise signal compared to a lower frequency range corresponding to the biological sounds.

A method of processing signals detected by an electronic stethoscope according to an embodiment of the current invention includes obtaining an auscultation signal from a body under observation with the electronic stethoscope, the auscultation signal including a target body sound; obtaining a noise signal including noise from an environment of the body; and obtaining a resultant signal by subtracting information from the auscultation signal, the subtracted information being based on at least a portion of the noise signal. The subtracted information is based more on higher frequency ranges of the noise signal compared to a lower frequency range corresponding to the biological sounds.

A non-transitory computer-readable medium comprising software is provided according to an embodiment of the present invention. The software, when executed by a computer, causes the computer to receive a first signal from an electronic stethoscope monitoring a body, the first signal including a target body sound; receive a second signal including noise; and obtain a resultant signal by subtracting information from the first signal. The subtracted information is based on at least a portion of the second signal, and is based more on higher frequency ranges of the second signal compared to a lower frequency range corresponding to the target body sound.

BRIEF DESCRIPTION OF THE DRAWINGS

Further objectives and advantages will become apparent from consideration of the description, drawings, and examples.

DETAILED DESCRIPTION

Figure 1:
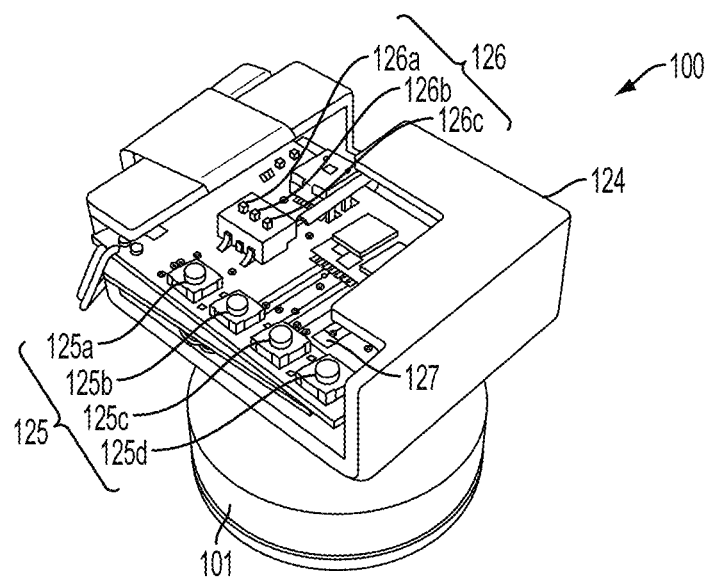
FIG. 1 shows an acoustic sensor assembly of an electronic stethoscope according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

An electronic stethoscope that can be used in some embodiments of the current invention is described in U.S. patent application Ser. No. 14/062,586, which was filed on Oct. 24, 2013, and which claims priority to U.S. Provisional Patent Application No. 61/718,034, which was filed on Oct. 24, 2012, and in International Application PCT/US2013/066647, which was filed on Oct. 24, 2013, all of which are incorporated herein by reference in their entireties.

Embodiments of the invention include a digital stethoscope and/or software algorithm for denoising of lung sound recordings. The software algorithm can enhance the quality of lung sounds (or other body sounds) recorded using a digital stethoscope mounted with an external microphone. The sounds acquired by the stethoscope can be recorded or processed in real-time or near real-time. The algorithm may operate by removing unwanted noise interferences such as background talk, patient crying, room noises, etc. The software algorithm is uniquely tailored to improving the quality of lung sounds (or other body sounds) by adaptively adjusting to the surrounding noise profile. Generic sound enhancement algorithms are non-specific to lung signals, for example, and result in undesirable corruptions of the lung signals. Although lung sounds are specifically discussed herein, embodiments of the invention are not limited to lung sounds, and may be used when detecting other body sounds.

As used herein, the term "real-time" is intended to mean that the sounds can be acquired, recorded, and/or processed according to various embodiments of the invention during use of the auscultation system. In other words, any noticeable time delay between acquiring and recording or processing the sounds is sufficiently short for the particular application at hand. In some cases, the time delay can be so short as to be unnoticeable by a user listening to processed sounds from the auscultation device.

According to some embodiments, an automated, multi-band denoising system and method for improving the quality of auscultation signals against heavy background contaminations is provided. The system and method can include an algorithm that can be employed with a multi-microphone setup, including a simple two-microphone setup, to dynamically adapt to the background noise and suppress contaminations while successfully preserving the lung sound content. Some embodiments are refined to offset maximal noise suppression against maintaining the integrity of the lung signal, particularly its unknown adventitious components that provide the most informative diagnostic value during lung pathology.

Figure 2:
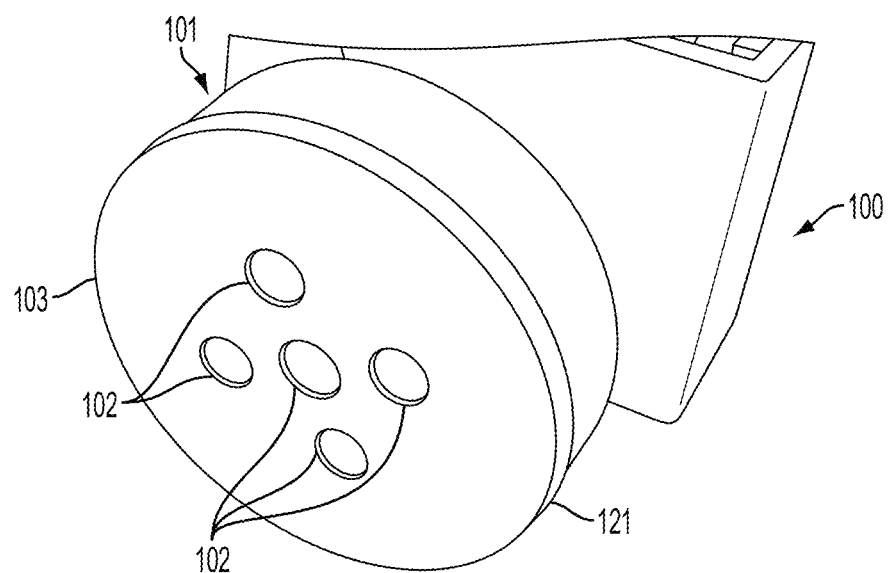
FIG. 2 shows a microphone array on the bottom of an acoustic sensor assembly according to an embodiment of the current invention.
Figure 6:
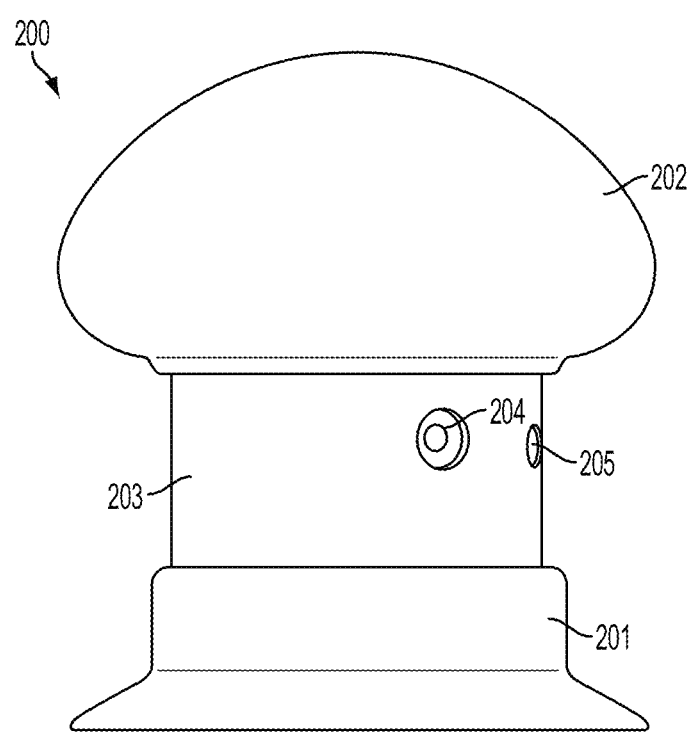
FIG. 6 shows an acoustic sensor assembly of an electronic stethoscope according to an embodiment of the current invention.
Figure 7:
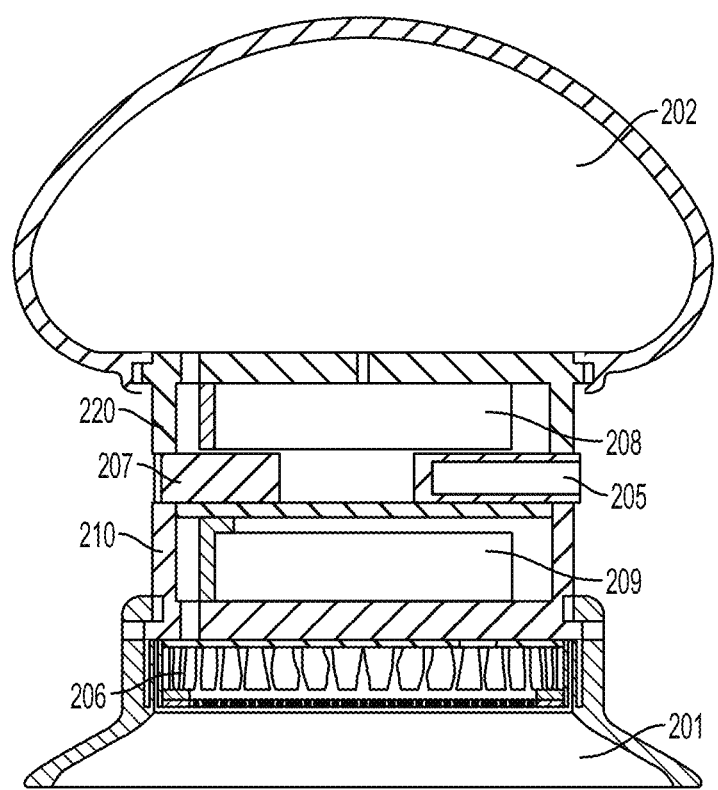
FIG. 7 shows a cross-section of the embodiment of the acoustic sensor assembly shown in FIG. 6.

FIGS. 1 and 2 show an embodiment of an electronic stethoscope according to an embodiment of the current invention. FIGS. 6 and 7 show another embodiment of an electronic stethoscope according to an embodiment of the current invention. However, the electronic stethoscopes shown in FIGS. 1, 2, 6, and 7 are shown by way of example, and embodiments of the current invention can be implemented with numerous types of electronic stethoscopes, whether specifically designed according to an embodiment of the invention, or adapted for use with the systems, methods, and software of embodiments of the invention.

Embodiments of the current invention were developed to detect body sounds such as the lungs, for example, as opposed to existing denoising algorithms that were developed mainly for speech sounds. In embodiments of the current invention, a number of parameters and design choices can be used to tailor the work to lung sounds. These parameters include choice of the time window, splitting of frequency bands, oversubtraction factor and additional band-subtraction factors, spectral floor parameter, smoothing of the noise spectrum. The algorithm according to some embodiments also can include a pre-processing step to address clipping distortion issues and a post-processing step to eliminate recording intervals that contain no information related to lung sounds.

Lung sounds that are recorded by a digital stethoscope are typically subject to a great number of noise contaminations from the surrounding environment. No methods currently exist to improve quality of these signals and existing methods of denoising result in undesirable corruption that make the auscultation signal loose its clinical value. The systems, methods, and software according to embodiments of the present invention are tailored for use with digital stethoscopes equipped with an external microphone, and improves the quality of the lung signal recorded by cancelling any distortions or noise from the surrounding sounds.

Embodiments of the current invention allow noise and unwanted body sounds to be reduced by digital signal processing (DSP). DSP can be combined with the other mechanical techniques according to some embodiments of the current invention. For example, the detection and analysis of a desired signal can be contaminated by noise at three points: at the stethoscope head, through the hose, and at the ear of the user. According to some embodiments of the current invention, noise at all three points can be mitigated by, for example, better coupling to the body, elimination of a rubber hose, and by using noise cancelling headphones at the listener's ear. In some embodiments, DSP can be used not only to reduce unwanted sounds, but to help identify various sounds.

Accordingly, some embodiments of the current invention can provide systems and methods to monitor and record sounds from the human body, including heart, lung, and other emitted sounds in the presence of high noise using multi-sensor flexible auscultation instruments used to detect a desired signal, as well as methods to seal the pickup device of the instrument to the body to reduce external noise from contaminating the desired signal. DSP according to some embodiments can include noise cancelling techniques by processing external noise picked up by a microphone exposed to noise near the auscultation instrument. Additional DSP to classify differences between subjects can be employed according to some embodiments to help identify potential problems in the lung or other sound emitting organs.

Embodiments that include electronic stethoscope are discussed below. However, embodiments of the invention are not limited to the structural embodiments provided herein. Embodiments may also include systems, methods, and software for detecting, analyzing, and processing signals, rather from live, real-time or near-real-time signals or from recorded signals.

FIG. 1 shows an electronic stethoscope 100 according to an embodiment of the current invention.

The electronic stethoscope 100 includes an acoustic sensor assembly 101 having a plurality of microphones 102 arranged in an acoustic coupler 103 to provide a plurality of pick-up signals. Piezoelectric polymers may also be used in place of the plurality of microphones. The electronic stethoscope 100 also includes a detection system 104 and an output system 105. The detection system 104 communicates with the acoustic sensor assembly 101 and combines the plurality of pick-up signals to provide a detection signal 106. The output system 105 communicates with the detection system 104. The acoustic coupler 103 is made of a compliant material 121 that forms an acoustically tight seal with a body under observation.

The phrase "acoustically tight" seal in reference to the acoustic coupler means that it obtains a decrease in the amount of ambient noise from outside the body under observation compared to a conventional stethoscope, such as a non-compliant metal component.

The plurality of microphones 102 can include any number of microphones. FIG. 2 shows an embodiment having five microphones. However, the plurality of microphones can contain more or fewer microphones. For example, six microphones may be used. The plurality of microphones 102 may be electret microphones, or some other type of microphone suitable for auscultation, for example. The plurality of microphones can be replaced by an inverted electret microphone, or piezo-active polymers such as polyvinylidene-fluoride (PVDF), or poly(γ-benzyl-L-glutamate) (PBLG).

In another embodiment, two microphones can be used: one for detecting the desired signal from the patient, and one for detecting environmental noise. These two microphones can be incorporated into a specifically designed unit, or a pre-existing stethoscope can be adapted to have the second microphone placed on or near it for the detection of environmental noise.

As shown in FIG. 2, the plurality of microphones 102 is placed within the compliant material 121. Accordingly, the microphones may be positioned securely while the stethoscope is guided over the skin of a patient. The compliant material 121 may be, for example, rubber. However, the compliant material 121 is not limited to rubber, and may be any polymer, composite, or other material suitable for achieving an acoustically tight seal for the acoustic coupler 103.

Figure 3:
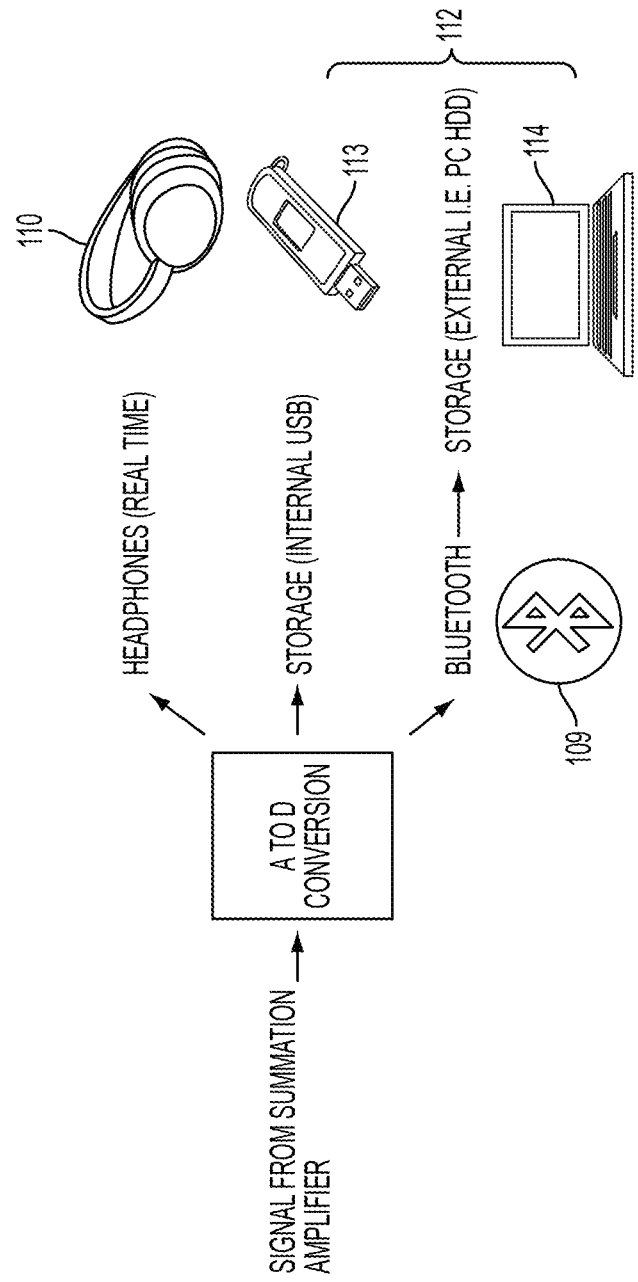
FIG. 3 is a schematic illustration of various embodiments of the current invention that have differently configured output systems, including (1) headphones, (2) storage on a portable USB drive, or (3) storage on a computer connected to the electronic stethoscope via Bluetooth.

The detection system 106 may also include a wireless transmitter 107 and the output system may correspondingly include a wireless receiver 108. Thus, a wireless communication link 109 may be provided between the detection system 106 and the output system 107. The wireless transmitter 107 may be a radio frequency wireless transmitter, including, for example, a Bluetooth radio frequency wireless transmitter, as shown in FIG. 3. Additionally, the wireless receiver 108 may be a radio frequency wireless receiver, including, for example, a Bluetooth radio frequency wireless receiver.

As shown in FIG. 3, the output system 105 may include headphones 110, which may include the wireless receiver 108 to provide the wireless communication link 109 between the detection system 104 and the headphones 110. Thus, the headphones 110 may be a wireless-type headphone, including a Bluetooth-enabled headphone. Alternatively, the detection system 106 and the headphones 110 may communicate over a hard-wired communication link 111 using at least one of an electrical wire or an optical fiber, for example.

The output system 105 may also include a data storage device 112. The data storage device 112 may be comprised of any known storage device, including a removable data storage component 113 or a computer 114.

At least one of the plurality of microphones 102 may be arranged external to the acoustic coupler 103 to receive external acoustic signals from sources that are external to the body under observation. At least one of the detection system 104 and the output system 105 may be further configured to perform a correction of the detection signal 106 based on the external acoustic signals. The correction may include at least partially filtering the external acoustic signals from the detection signal 106. The correction may be based, for example, on a waveform characteristic of the external acoustic signal.

The output system 105 may include a data processing system 116 configured to perform an identification of at least one of a physical process and a physiological condition of the body based on the detection signal 106. The identification may be based, for example, on at least one of a temporal characteristic and a spectral characteristic of the detection signal 106.

The output system 105 may be further configured to provide aural or visual feedback to a user of the electronic stethoscope 100.

According to an embodiment, the electronic stethoscope 100 includes an acoustic sensor assembly 101 including a microphone 117 arranged in an acoustic coupler 103 to provide a detection signal 106 from a body under observation, and a microphone 115 arranged external to the acoustic coupler 103 to receive external acoustic signals from sources that are external to the body under observation. The electronic stethoscope 100 of this embodiment also includes a detection system 104 configured to communicate with the acoustic sensor assembly 101 and an output system 105 configured to communicate with the detection system 104. At least one of the detection system 104 and the output system 105 is further configured to perform a correction of the detection signal 106 based on the external acoustic signals.

The correction may at least partially filter the external acoustic signals from the detection signal 106. In addition, the correction may be based on a characteristic of at least one of the external acoustic signal and the detection signal 106.

An embodiment of the current invention is a method for processing signals detected by an electronic stethoscope 101 from a body under observation. The method comprises obtaining a signal captured by the electronic stethoscope 101, identifying a part of the signal that corresponds to at least one of a noise external to the body under observation and an internal sound of the body, and optionally removing at least a portion of the part of the signal. The part of the signal can be identified according to at least one of a frequency characteristic and a time characteristic of the part of the signal. The part of the signal can also be identified based on a reference signal. In some embodiments, the signal can be obtained from a recording or in real-time from a stethoscope used on a patient.

"Identifying" as used in the method of this embodiment may include recognizing and/or labeling a source of the part of the signal, or merely differentiating that part of the signal from some remainder of the signal.

The method for processing signals may further include performing a discrete wavelet transformation of the signal. The transformation can include filtering the signal in a number of steps. Each step includes (1) applying a high-pass filter and a low-pass filter to the signal, (2) obtaining a first coefficient and a second coefficient as a result of applying the high-pass filter and the low-pass filter, respectively, and (3) downsampling the signal after applying the high- and low-pass filters. The transformation also includes transforming the signal based on at least one the first coefficient and the second coefficient obtained from at least one of the steps of filtering. For example, the transformation may include or exclude only the first coefficient from a particular filtering level, or only the second coefficient from a particular filtering level, or a combination of the first and second coefficients from one or more particular filtering levels.

Various forms of signal processing, including those for noise cancellation and filtering and/or identifying sounds in the signal, can be automated in either the electronic stethoscope or a device storing the signal detected by the electronic stethoscope. Such an automated system can be used to aid in detecting and identifying physical processes or physiological conditions within a body. For example, based on lung sounds detected by the electronic stethoscope 100, an automated system can be used to detect respiratory illnesses, classify them into clinical categories using specific characteristics and features of lung sounds, and diagnose the severity or cause of a possible pulmonary dysfunction. In this, the advantages provided by the electronic stethoscope 100 as well as the signal processing can compensate for untrained health care providers, subjectivity in interpreting respiratory sounds, or limitations of human audition.

Figure 5:
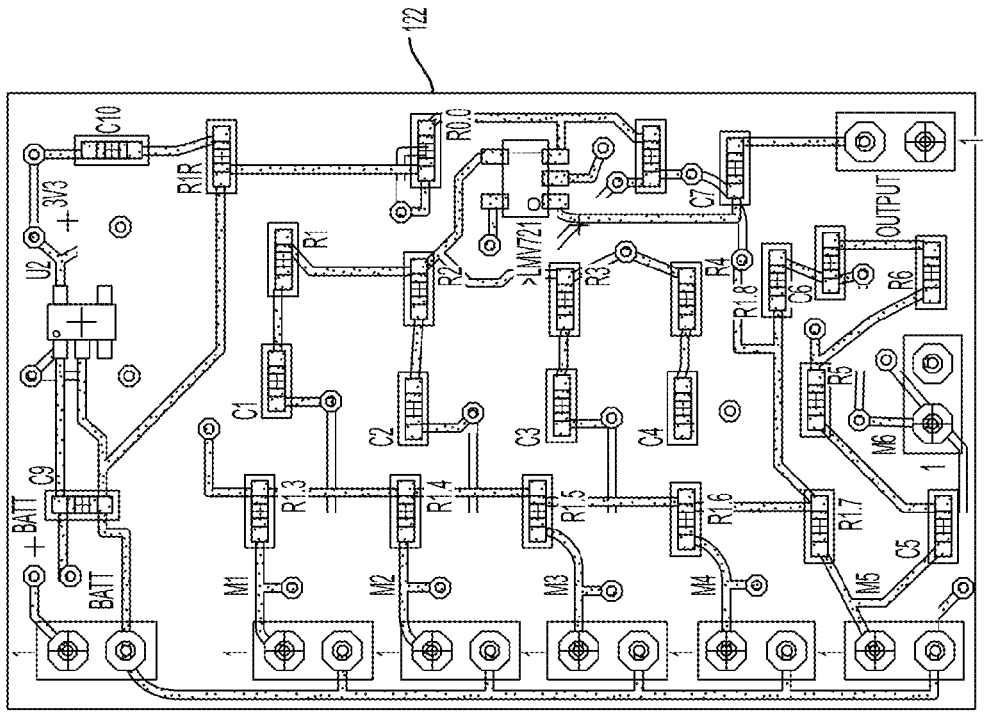
FIG. 5 shows a schematic of an example of a summation amplifier circuit board according to an embodiment of the current invention.

FIG. 5 shows a schematic of an example of a circuit board for a summation amplifier 122 according to an embodiment. Wires from the batteries used to power the electronic stethoscope 100, including the plurality of microphones 102, are fed to the summation amplifier 122 and soldered directly onto the summation amplifier 122. On the summation amplifier 122, the signals from each of the plurality of microphones 102 are combined and amplified. The amplification may be at a gain of about 1.5, for example. The signal is shielded with a decoupling capacitor on the summation amplifier 122 before going to any number of output mechanisms. In one embodiment, for example, the signal goes to the Bluetooth adapter circuit 123 shown in FIG. 4. Once the signal arrives at the Bluetooth adapter circuit 123, it goes to a small Bluetooth adapter that can stream it wirelessly to a standard A2DP stereo compatible Bluetooth headset or computer. A signal sent via Bluetooth can thus be recorded, or sent directly to a jack of a noise cancelling headphone 110 for live playback of the signal.

In some embodiments, a microcontroller (not shown) can be incorporated into the electronic stethoscope 100 so that recordings can be stored directly on the device or on a portable USB stick 113. Circuitry in alternative embodiments also can support built-in signal processing algorithms that may help a medical officer make a diagnosis.

The following is a description of the operation of the embodiment of the electronic stethoscope 100 shown in FIG. 1. The top of a housing 124 of the electronic stethoscope 100 shown in FIG. 1 is cut out to allow a user access to switches 125 and 126 on the top of the electronic stethoscope 100. The housing 124 may be sanded or filleted to remove sharp edges. Other embodiments may use a different housing which can incorporate an LED screen. The embodiment in FIG. 1 has push button switches 125 (four shown as 125a-125d) and a three-pin switch 126 that allow the user to control the device. However, different numbers and configurations of switches are possible.

Figure 4:
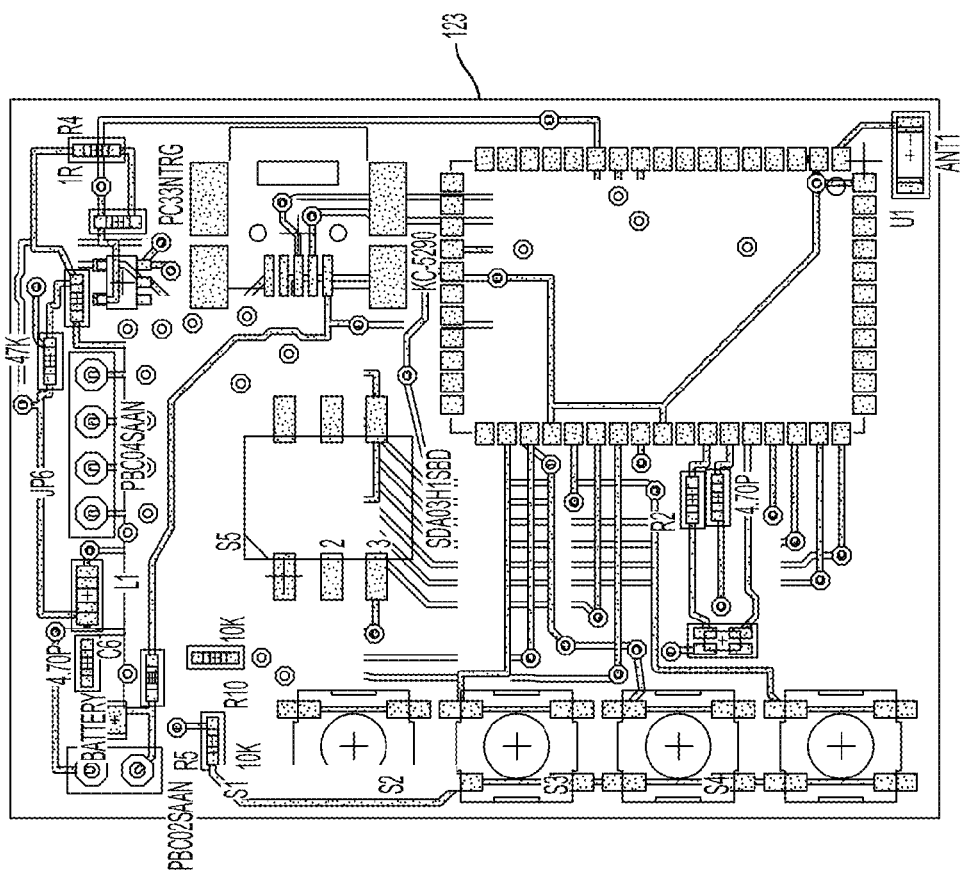
FIG. 4 shows an example of a Bluetooth adapter circuit board according to an embodiment of the current invention.

In order to provide power to both circuit boards shown in FIGS. 4 and 5, the user first slides pin 3 126c of the 3-pin switch 126. Holding down the first push button switch 125a for at least 2.5 seconds allows the user to turn the device on or off. Once the device turns on it immediately searches for a headset to connect to and a light emitting diode (LED) 127 blinks rapidly. The electronic stethoscope 100 in FIG. 1 runs on a single battery source. However, the device can also receive power and/or recharge the battery via a USB port (not shown). The USB port can also be used to download firmware updates to the Bluetooth adapter.

FIG. 6 shows an electronic stethoscope 200 according to another embodiment of the current invention. The electronic stethoscope 200 may include a bottom cover 201, top cover 202, and electronics case assembly 203. The electronic stethoscope 200 may also include a variety of controls, ports, and indicators, such as an LED 204 and headphone jack 205, as shown on the electronics case assembly 203 in FIG. 6.

The electronic stethoscope 200 of FIG. 6 is shown in cross-section in FIG. 7 revealing the interior of the electronics case assembly 203 and the transducer 206. The electronics case assembly 203 can house electronics 208 and batteries 209. As shown in FIG. 7, the electronics case assembly 203 can also include a power jack 207.

The interior of the bottom cover 201 and top cover 202 can be, for example, hollow, as shown in the embodiment of FIG. 7. In one embodiment, it is contemplated that a negative pressure can be created within at least the bottom cover 201 when the electronic stethoscope 200 is in use and the bottom cover 201 is in contact with a patient. In such a case, auscultation can be performed using a hands-free operation of the electronic stethoscope 200, thereby eliminating noise from hand movements during data collection. Such an embodiment may be useful when using the device with infants, for example.

In one embodiment, the bottom cover 201 and top cover 202 may be made from urethane rubber, for example, and both covers 201, 202 may be securely connected to the electronics case assembly 203.

Figure 8:
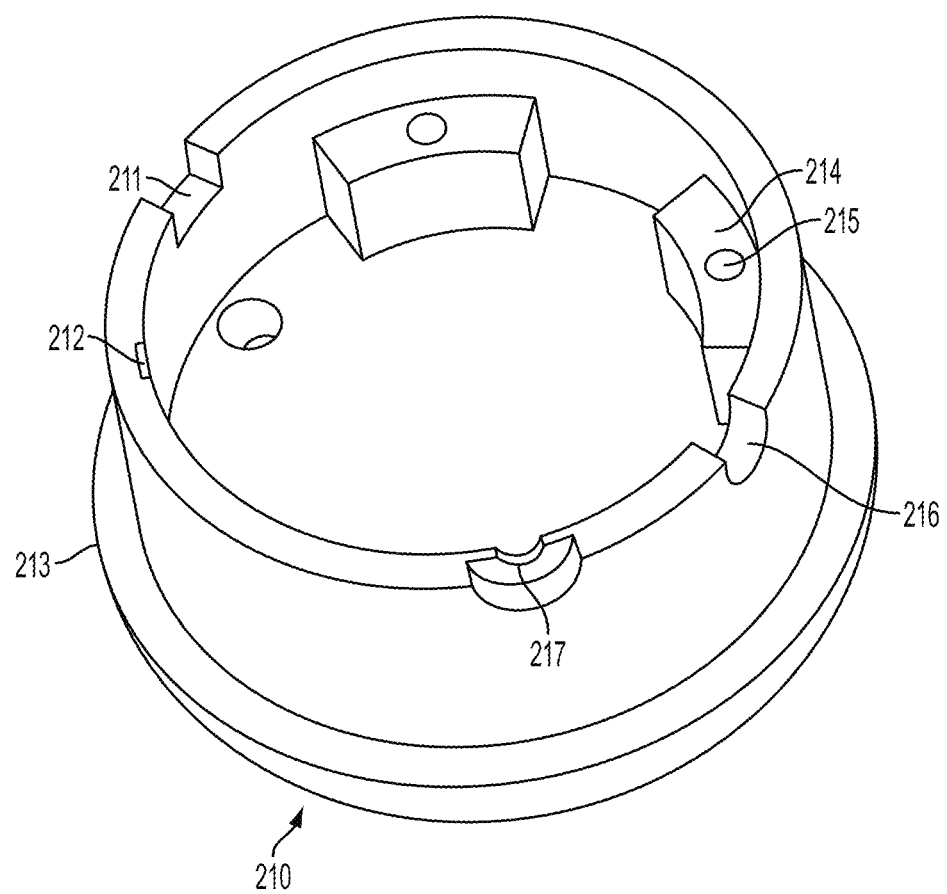
FIG. 8 shows an example of a bottom of an electronics case in the acoustic sensor assembly of FIG. 6.

In addition, the electronics case assembly 203 can be made of a bottom electronics case 210 and a top electronics case 220. FIG. 8 shows an example of the bottom electronics case 210, which includes a headphone jack hole 216, an LED hole 217, and a power jack slot 221. The bottom electronics case 210 may also include a trim pot slot 212 to accommodate a trim pot (not pictured) in the electronics within the electronics case assembly 203. Within the bottom electronics case 210 can be one or more hubs 214 and each hub 214 may have a screw hole 215. It is understood that a hole for accommodating some other suitable attachment member other than a screw can be provided. The bottom of the bottom electronics case 210 can include a connection ring 213.

Figure 9:
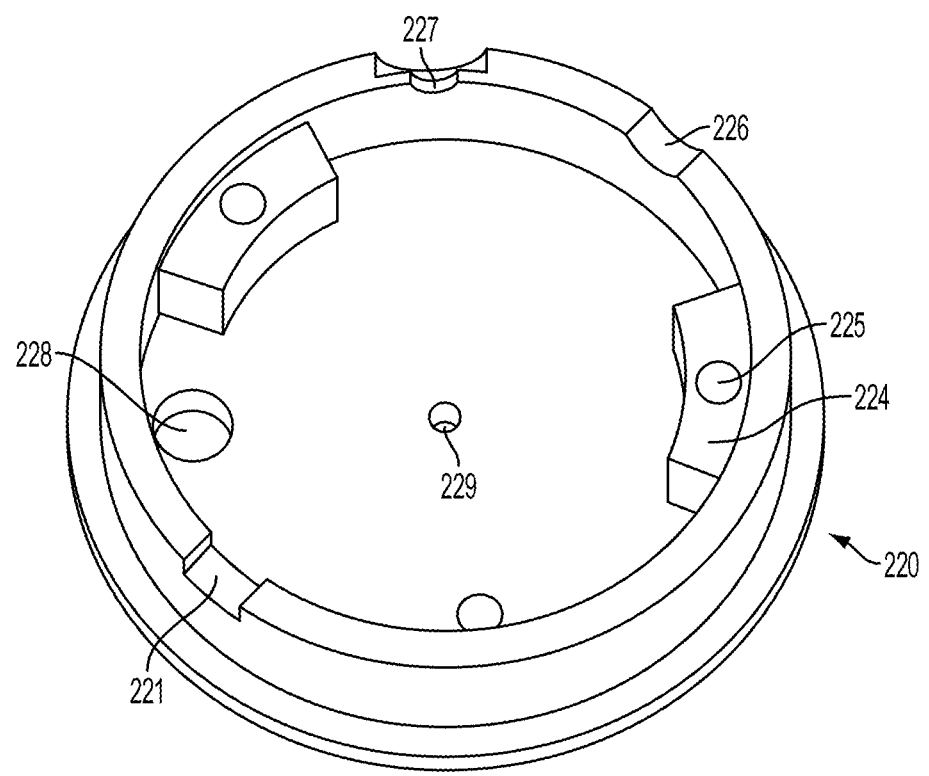
FIG. 9 shows an example of a top of an electronics case in the acoustic sensor assembly of FIG. 6.

The top electronics case 220, an example of which is shown in FIG. 9, can include a headphone jack hole 226, an LED hole 227, and a power jack slot 221 corresponding to those in the bottom electronics case 210 shown in FIG. 8. Alternatively, holes for an LED, power jack, and headphone jack can be solely within either one of the bottom electronics case 210 and top electronics case 220. Similar to the bottom electronics case 210, the top electronics case 220 may include one or more hubs 224 and screw holes 225. The top electronics case 220 also may include at least one air hole 228 and a switch leg hole 229.

The air hole 228 may be provided to put the interior of the bottom cover 201 and the top cover 202 in fluid communication with each other. In this way, negative pressure can be created between the electronic stethoscope 200 and a body under observation. For example, the negative pressure can be created by an operator of the electronic stethoscope 200 squeezing the top cover 202 to force air out through the air hole 228 and unsqueezing the top cover 202 when the electronic stethoscope is applied to a body under observation. The relative negative pressure is thus created within the bottom cover 201 via the air hole 228 and the top cover 202.

Figure 10:
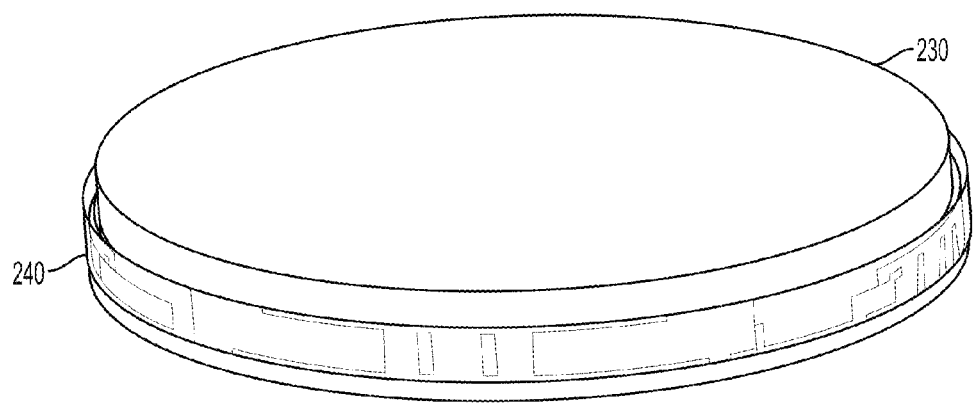
FIG. 10 shows a housing of the transducer using in the acoustic sensor assembly of FIG. 6.
Figure 11:
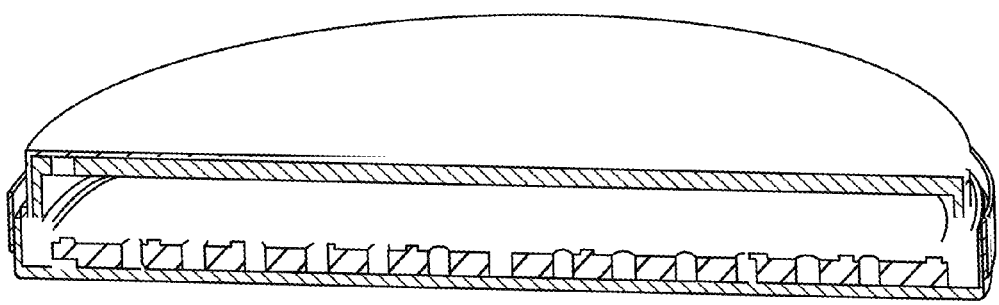
FIG. 11 shows a cross-section of the housing of FIG. 10 and the transducer.
Figure 12:
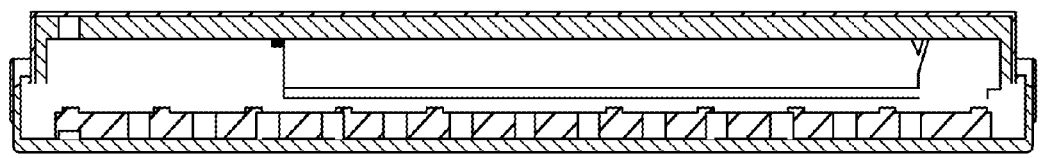
FIG. 12 shows a second cross-section of the housing of FIG. 10 and the transducer.

As shown in FIG. 7, the transducer 206 may be positioned below the electronics case assembly 203 and within the bottom cover 201, for example. The transducer 206 may further be contained within a transducer cover 230, as shown in FIG. 10. A cross-section of the transducer 206 is shown in FIGS. 11 and 12. The details revealed in these cross-sections are discussed below with respect to FIG. 13, which shows a close-up of the cross-section of the transducer 206.

Figure 13:
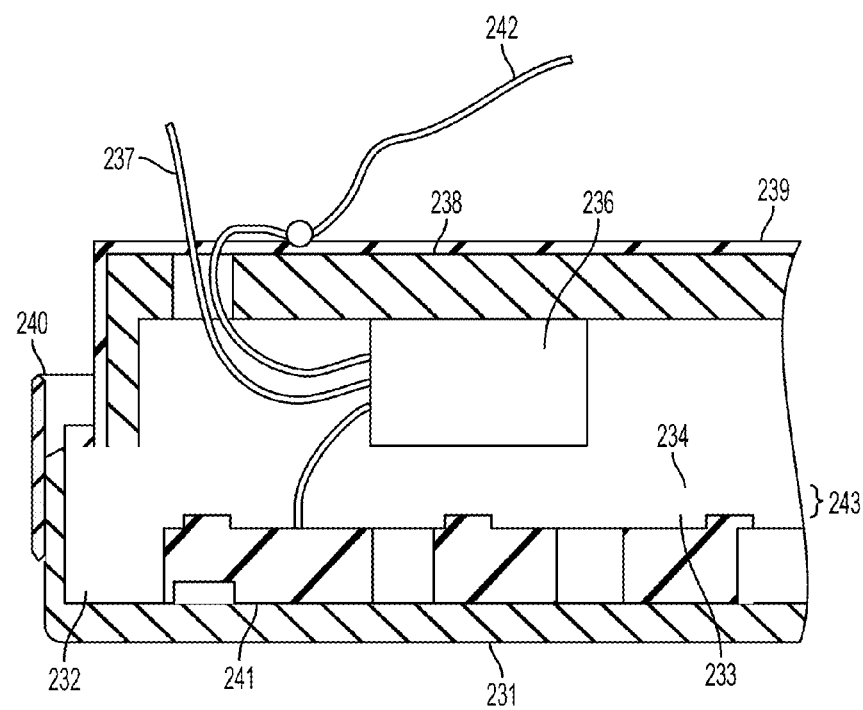
FIG. 13 shows a close-up cross-section of the transducer used in the acoustic sensor assembly of FIG. 6.

As discussed above, transducer 206 of the electronic stethoscope 200 may be in the form of an electret microphone as shown in FIG. 13. Generally, a diaphragm of a microphone exposed to the environment is covered by a dust cap to prevent foreign matter from contaminating the performance. In the case where such a diaphragm is distorted by external interference, such as pressing the microphone against the human body to collect body sounds such as lung and heart sounds, the diaphragm may collapse or the sensitivity may change depending on how much force is applied. To eliminate these effects, an embodiment of the current invention uses an inverted electret microphone where the back plate is exposed to the patient, and since the back plate is a stiff material, the sensitivity of the electret microphone is independent of the force applied. The transducer 206 in FIG. 13 shows an example of such an electret microphone.

The transducer 206 includes microphone cover 231 that may be, for example, a nitrile rubber cover, or another polymer, rubber, or other material. Behind the microphone cover 231 is a back electrode 241 that is connected to a field-effect transistor (FET) 236 housed within a microphone case 238. In one embodiment, the microphone case 238 may be the product of a 3D printer. A drain 237 and ground 242 may be fed from the FET 236 through a hole in the microphone case 238, with the ground contacting a ground surface 239 positioned on top of the microphone case 238. The ground surface 239 can be, for example, aluminum foil.

The back electrode 241 can be made from a variety of materials, including, for example, stainless steel. A side of the back electrode 241 that is opposite to the microphone cover 231 is bordered by a multi-layer structure 243 including, for example, a polymer 233, fluorinated ethylene propylene (FEP) 232, and aluminum 234.

The transducer 206 may also be surrounded by a wrap 240, such as a PVC shrink wrap, for example.

Figure 14:
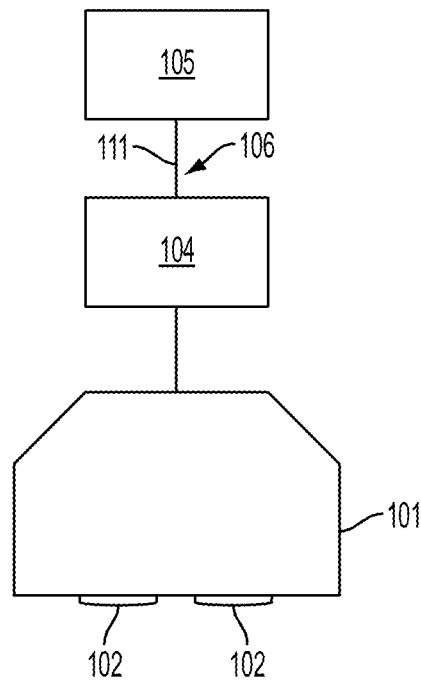
FIG. 14 shows a schematic of an electronic stethoscope according to an embodiment of the current invention.
Figure 15:
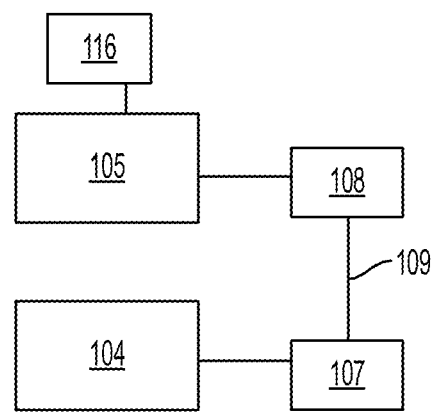
FIG. 15 shows a schematic of a detection system and output system of an electronic stethoscope according to an embodiment of the current invention.

FIGS. 14 and 15 show a schematic of an electronic stethoscope and detection and output system according to some embodiments of the current invention.

As described in the following examples, a team of clinical experts evaluated and confirmed that the quality of the lung sound processed through an embodiment of a system and method using an algorithm is noticeably improved relative to the original non-processed signal.

EXAMPLES

The following examples include examples of embodiments of the present invention. The examples are not intended to limit the scope of the present invention.

Example 1

I. Example Overview

In an example of an embodiment, an algorithm was applied to digital recordings obtained in the field from a busy clinic in West Africa and evaluated using objective signal fidelity measures and perceptual listening tests performed by a panel of licensed physicians. A strong preference of the enhanced sounds was revealed. The strengths and benefits of the system and method of this embodiment lie in the simple automated setup and its adaptive nature, both fundamental conditions for everyday clinical applicability. Although this example applies to recordings, the system and methods of the embodiment of this example, as well as other embodiments, can be simply extended to a real-time implementation, and integrated with lung sound acquisition protocols.

According to this example embodiment, multiband spectral subtraction was used to address noise contaminations in busy patient care settings, where prominent subject-centric noise and room sounds typically corrupt the recorded signal and mask the lung sound of interest. The setup employed a simple digital stethoscope with a mounted external microphone capturing the concurrent environmental or room noise. The algorithm of the current example was focused on two parallel tasks: 1) suppressing the surrounding noise; 2) preserving the lung sound content. The use of spectral subtraction as a signal denoising approach in some embodiments is specifically designed for the application at hand in at least two ways. First, for example, although the signal of interest (i.e., lung sounds) has relatively well-defined characteristics, unknown anomalous sound patterns reflecting lung pathology complicate the analysis of the obtained signal. These adventitious patterns vary from quasi-stationary events, such as wheezes, to highly transient sounds, such as crackles. They are unpredictable, irregular patterns whose signal characteristics are not well defined in the literature. Yet, it may be desirable according to some embodiments for the processing to faithfully preserve these occurrences given their possible clinical and diagnostic significance. Second, noise is highly non-stationary and its signal characteristics differ in the degree of overlap with the signal of interest. Noise contaminations can include environmental sounds picked up in the examination room (chatter, phones ringing, fans, etc.), patient-specific noises (child cry, vocalizations, agitation), or electronic/mechanical noise (stethoscope movement, mobile interference).

The investigation of this example tried to balance the suppression of the undesired noise contaminations while maintaining the integrity of the lung signal along with its adventitious components. The multiband spectral scheme of this example carefully tuned the critical parameters in spectral subtraction in order to maximize the improved quality of the processed signal. The performance of the approach was validated by formal listening tests performed by a panel of licensed physicians, as well as objective metrics assessing the quality of the processed signal. The following sections II and III describe the theory and implementation details of the algorithm according to this example. Section IV discusses the formal listening experiment setup. Evaluation results are described in Section V, including comparisons to other methods. Section VI describes a general discussion of the approach of an embodiment according to this example.

II. Multiband Spectral Subtraction

Spectral subtraction algorithms have been widely used in fields of communication and speech enhancement to suppress noise contaminations in acoustic signals. The general framework behind these noise reduction schemes can be summarized as follows: let y(n) be a known measured acoustic signal of length N and assume that it comprises of two additive components x(n) and d(n), corresponding respectively to a clean unknown signal we wish to estimate and an inherent noise component which is typically not known. In many speech applications, the noise distortion is estimated from silent periods of the speech signal that are identified using a voice activity detector. Alternatively, the noise distortion can be estimated using a dual or multi-microphone setup, where a secondary microphone picks up an approximate estimate of the noise contaminant. The embodiment of this example employs the latter: a dual-microphone setup capturing both the internal signal coming from the stethoscope itself, and the external signal coming from a mounted microphone. In this example, the external signal is assumed to be closely related to the actual noise that contaminates the lung signal of interest, and shares its spectral magnitude characteristics with possibly different phase profiles due to their divergent traveling trajectories to the pickup microphones.

Here, noise is assumed to have additive effects on the desired signal and originate through a wide-sense stationary process. Without loss of continuity, the stationarity requirements for the noise process are alleviated, and a smoothly varying process whose spectral characteristics change gradually over successive short-time periods is assumed. In this example, such noise signal $d(n,\tau)$ represents the patient- or room-specific noise signal; $x(n,\tau)$ denotes the desired, unknown, clean lung sound information, free of noise contaminations; and $y(n,\tau)$ denotes the acoustic information captured by the digital stethoscope:

$$y(n,\tau)=x(n,\tau)+d(n,\tau) \quad (1)$$

where $\tau$ is used to represent processing over short-time windows $w(n)$. In other words, $x(n,\tau)=x(n)w(\tau-n)$ and similarly for $y(n,\tau)$ and $d(n,\tau)$. For the corresponding frequency-domain formulation, let $X(\omega,\tau)$ denote the discrete Fourier transform (DFT) of $x(n,\tau)$, implemented by sampling the discrete-time Fourier transform at uniformly spaced frequencies $\omega$. Letting $Y(\omega,\tau)$ and $D(\omega,\tau)$ be defined in a similar way for $y(n,\tau)$ and $d(n,\tau)$, Equation (1) becomes: $|Y(\omega,\tau)|e^{j\phi_y(\omega,\tau)}=|X(\omega,\tau)|e^{j\phi_x(\omega,\tau)}+|D(\omega,\tau)|e^{j\phi_d(\omega,\tau)}$. Short-term magnitude spectrum $|D(\omega,\tau)|$ can be approximated as $|\hat{D}(\omega,\tau)|$ using the signal recorded from the external microphone. Phase spectrum $\phi_d(\omega,\tau)$ can also be reasonably replaced by the phase of the noisy signal $\phi_y(\omega,\tau)$ considering that phase information has minimal effect on signal quality especially at reasonable signal-to-noise ratios (SNR) [14]. Therefore, the denoised signal can be formulated as $$\hat{X}(\omega,\tau)=(|Y(\omega,\tau)|-|\hat{D}(\omega,\tau)|)e^{j\phi_y(\omega,\tau)}. \quad (2)$$

The same formulation can be extended to the power spectral density domain by making the reasonable assumption that environmental noise $d(n,\tau)$ is a zero-mean process, uncorrelated with the lung signal of interest $x(n,\tau)$:

$$|\hat{X}(\omega,\tau)|^2=|Y(\omega,\tau)|^2-|\hat{D}(\omega,\tau)|^2 \quad (3)$$

Building on this basic spectral subtraction formulation to synthesize the desired signal, this design can be extend in a number of ways:
1) Extending the subtraction scheme into multiple frequency bands $$\{\omega_k\} \in [\omega_k^{min}, \omega_k^{max}].$$

This localized frequency treatment is especially helpful given the variable, unpredictable, and non-uniform nature of noise distortions that affect the lung recording. Looking back to Equation (3), the subtraction term $\hat{D}(\omega,\tau)$ can be weighted differently across frequency bands by constructing appropriate weighting rules ($\delta_k$) that highlight the most informative spectral bands for lung signals.
2) Altering the scheme to weight the subtraction operation across time windows and frequency bands by taking into account the current frame's SNR.
3) Reducing the residual noise in the signal reconstruction by smoothing $Y(\omega,\tau)$ estimate over adjacent frames.

Therefore, for frame $\tau$ and frequency band $\omega_k$, the enhanced estimated signal spectral density is given by $$|\hat{X}(\omega_k,\tau)|^2=|\bar{Y}(\omega_k,\tau)|^2-\alpha_{k,\tau}\delta_k|\hat{D}(\omega_k,\tau)|^2 \quad (4)$$

Bar notation $\bar{Y}(\omega_k,\tau)$ signifies a smooth estimate of $Y(\omega_k,\tau)$ over adjacent frames. $\alpha_{k,\tau}$ is an oversubtraction factor adjusted by the current frame's SNR, for each band $\omega_k$ and frame $\tau$. $\delta_k$ is a spectral weighting factor that highlights lower frequencies typically occupied by lung signals and penalizes higher frequencies where noise interference can spread. Partial noise can then added back to the signal using a weighing factor $\gamma_\tau \epsilon(0, 1)$ to suppress musical noise effects. The final estimate $\tilde{x}(n)$ is resynthesized using the inverse DFT and overlap and add method across frames:

$$|\tilde{X}(\omega_k,\tau)|^2=(1-\gamma_\tau)|\hat{X}(\omega_k,\tau)|^2+\gamma_\tau|\bar{Y}(\omega_k,\tau)|^2 \quad (5)$$

III. Methods

Lung signals were acquired using a Thinklabs ds32a digital stethoscope at 44.1-kHz rate, by the Pneumonia Etiology Research for Child Health (PERCH) study group [18]. Thinklabs stethoscopes used for the study were mounted with an independent microphone fixed on the back of the stethoscope head, capturing simultaneous environmental contaminations without any hampering of the physician's examination. Auscultation recordings were obtained from children enrolled into the PERCH study with either World Health Organization-defined severe and very severe clinical pneumonia (cases) or community controls without clinical pneumonia in a busy clinical setting in Basse, Gambia in West Africa. A total of 22 infant recordings among hospitalized pneumonia cases with an average age of 12.2 months (2-37 months) were considered. Following the examination protocol, nine body locations were auscultated for a duration of 7 s each. The last body location corresponded to a cheek position and is not used in this study.

Noise contaminations were prominent throughout all recordings in the form of ambient noise, mobile buzzing, background chatter, intense subject's crying, musical toys in the waiting room, power generators, vehicle sirens, or animal sounds. Patients were typically seated in their mothers' lap and were quite agitated, adding to the distortion of auscultation signal.

A. Preprocessing

All acquired signals were low-pass filtered with a fourth-order Butterworth filter at 4 kHz cutoff, downsampled to 8 kHz, and centered to zero mean and unit variance. Resampling can be justified by guidelines of the CORSA project of the European Respiratory Society, as lung sounds are mostly concentrated at lower frequencies.

A clipping distortion algorithm was then applied to correct for truncated signal amplitude (occurring when the microphone reached maximum acoustic input). Although clipped regions were of the order of a few samples per instance, they produced very prominent signal distortions. The algorithm identifies regions of constant (clipped) amplitude, and replaces these regions using cubic spline interpolation.

B. Implementation

The algorithm of this example employs a wide range of parameters that can significantly affect the reconstructed sound quality. An initial evaluation phase using informal testing and visual inspection reduced the parameter space. The preliminary assessment of the algorithm suggests that 32 frequency bands were adequate, using frequency-domain windowing to reduce complexity. Since the algorithm operates independently among bands, their boundaries can affect the final sound output. Two ways of creating the subbands were explored: 1) logarithmic spacing along the frequency axis and 2) equi-energy spacing. The latter spacing corresponds to splitting the frequency axis into band regions containing equal proportions of the total spectral energy. Other band splitting methods were excluded from analysis after the initial assessment phase.

The weighing among frequency bands, regulated by factor $\delta_k$ in Equation (4), can be an important factor related to the frequency binning of the spectrum. Since interfering noise affects the spectrum in a nonuniform manner, this nonlinear frequency-dependent subtraction was imposed to account for different types of noise. It can be thought of as a signal-dependent regulator, taking into account the nature of the signal of interest. Lung sounds are complex signals comprised of various components: normal respiratory sounds typically occupy 50-2500 Hz, tracheal sounds reach energy contents up to 4000 Hz, and heart beat sounds vary within 20-150 Hz. Finally, wheeze and crackles, the commonly studied adventitious (abnormal) events, typically have a range of 100-2500 and 100-500 Hz, respectively. Other abnormal sounds like stridor, squawk, low-pitched wheeze or cough, all exhibit a frequency profile below 4 kHz. The motivation for appropriately setting factor $\delta_k$ is to minimize distortion of lung sounds that typically occupy low frequencies and penalize noise occurrences with strong energy content at high frequencies. The analysis performed for this example suggested two value sets for parameter $\delta_k$ in Table I. In logarithmic spacing, sub-bands $F_{17}$, $F_{25}$, $F_{26}$, and $F_{27}$ correspond to 80, 650, 850, and 1100 Hz, respectively. In equi-energy spacing, $F_m$ corresponds to the $m^{th}$ sub-band whose frequency ranges are signal dependent; $F_{17}$, $F_{25}$, and $F_{26}$ roughly correspond to 750, 2000, and 2300 Hz.

Comparing the proposed sets, $\delta_k^{(1)}$ resulted in stronger suppression of high-frequency content.

TABLE I

Two proposed sets of values for $\delta_k$.

| $f_k$ band range | $\delta_k^{(1)}$ value | $\delta_k^{(2)}$ value |
|---|---|---|
| $(0, F_{17}]$ | 0.01 | 0.01 |
| $(F_{17}, F_{25}]$ | 0.015 | 0.02 |
| $(F_{25}, F_{26}]$ | 0.04 | 0.05 |
| $(F_{26}, F_{27}]$ | 0.2 | 0.7 |
| else | 0.7 | 0.7 |

This nonlinear subtraction scheme was further enforced by the frequency-dependent oversubtraction factor $\alpha_{k,\tau}$, defined in Equation (6), which regulates the amount of subtracted energy for each band, using the current frame's SNR. Larger values were subtracted in bands with low a posteriori SNR levels, and the opposite was true for high SNR levels. This way, rapid SNR level changes among subsequent time frames could be accounted for. On the other hand, such rapid energy changes were not expected to occur within a frequency band, considering the natural environment where recordings took place. Thus, the factor $\alpha_{k,\tau}$ could be held constant within bands. Such frame-dependent SNR calculations could also remedy for a type of signal distortion known as musical noise, which can be produced during the enhancement process.

$$\alpha_{k,\tau} = \begin{cases} 4.75: & SNR_{k,\tau} < -25 \\ 4 - \frac{3SNR_{k,\tau}}{20}: & -25 \leq SNR_{k,\tau} \leq 40 \\ 1: & SNR_{k,\tau} > 40 \end{cases} \quad (6)$$

$$SNR_{k,\tau} = 10\log_{10}\left(\sum_{\omega \in \omega_k} |\overline{Y}(\omega, \tau)|^2 / \sum_{\omega \in \omega_k} |\hat{D}(\omega, \tau)|^2\right)$$

The window length for short-time analysis of the signal was another crucial parameter that can result in noticeable artifacts, since a long-time window might violate the stationarity assumptions made in Section II. Following the initial algorithm assessment phase, two ways of short-time processing are proposed in this example: 1) 50-ms window (N=400) and 90% overlap; and 2) 80-ms window (N=640) with 80% overlap. Hamming windowing w(n) was applied in the time waveform to produce all frames. Negative values possibly arising by Equation (4) were replaced by a 0.001% fraction of the original noisy signal energy, instead of using hard thresholding techniques like half-wave rectification.

Finally, the enhancement factor $\gamma_\tau$ for frame $\tau$ in Equation (5) was an SNR-dependent factor and was set closer to 1 for high SNRτ, and closer to 0 for low SNR$_\tau$ values. For the calculation of $\overline{Y}((\omega_k, \tau))$, the smooth magnitude spectrum was obtained by weighting across ±2 time frames, given by | $\overline{Y}(\omega_k, \tau)| = \Sigma_{j=-2}^{2}$ W(j)|Y$_{\tau-j}$ ($\omega_k$)| with coefficients W=[0.09, 0.25, 0.32, 0.25, 0.09].

In Table I, the values for $\delta_k^{(1)}$, for example, were chosen as optimal values within various ranges in this example. For $f_k \leq F_{17}$, the optical/chosen value was 0.01. Although there was no noticeable difference for lower values, a value greater than 0.2 for $\delta_k^{(1)}$ resulted in significant deterioration of soft breathing sounds. For $F_{17} \leq f_k \leq F_{25}$, a value less than 0.01 did not affect sound events signifying a disease, but noise at lower frequencies comes through the algorithm (e.g., background chatter). On the other hand, a value greater than 0.2 resulted in significant deterioration of breaths and a less pleasant sound. The optical/chosen value was 0.015. For $F_{25} \leq f_k \leq F_{26}$, noise would still flow in for a value less than 0.01 (e.g., unsuccessful suppression of cry harmonics), and a value greater than 0.4 had better suppression of noise by a less pleasant sound. The optimal/chosen value in this range was 0.04. For $F_{26} \leq f_k \leq F_{27}$, values less than 0.1 would still allow noise in (e.g., unsuccessful suppression of cry harmonics), and values greater than 0.5 had better noise suppression but a less pleasant or unnatural sound. The optimal/chosen value was 0.2 for this range. For other frequency bands, an optimal/chosen value was 0.7 in this example. At less than 0.3, noise would still flow in (e.g., unsuccessful suppression of cry harmonics) and at greater than 0.8 there was better suppression of noise but a less pleasant or unnatural sound.

C. Post-Processing

Typically, time intervals where the stethoscope is in poor contact with the subject's body tended to exhibit insignificant or highly suppressed spectral energy. After the application of the enhancement algorithm, intervals with negligible energy below 50 Hz were deemed uninformative and removed. A moving average filter smoothed the transition edges.

IV. Human Listener Experiment

The listening experiment was designed with a two-fold purpose: 1) evaluate the effectiveness of the enhancement procedure and 2) evaluate the effect of the proposed parameters including frequency band binning, window size, and customized band-subtraction factor $\delta_{k,\tau}$ on the perceived sound quality.

A. Participants

Eligible study participants were licensed physicians with significant clinical experience auscultating and interpreting lung sounds from children. A total of 17 physicians (6 pediatric pulmonologists and 11 senior pediatric residents) were enrolled, all affiliated with Johns Hopkins Hospital in Baltimore, Md., USA, with informed consent, as approved by the IRB at the Johns Hopkins Bloomberg School of Public Health, and were compensated for participation.

B. Setup

The experiment took place in a quiet room at Johns Hopkins University and was designed to last for 30 min, including rest periods. Data recorded in the field in the Gambia clinic were played back on a computer to participants in the listening experiment. Participants were asked to wear a set of Sennheiser PXC 450 headphones and listen to 43 different lung sound excerpts of 3 s duration each. The excerpts originated from 22 distinct patients diagnosed with World Health Organization-defined severe or very severe pneumonia. For each excerpt, the participant was presented with the original unprocessed recording, along with four enhanced versions A, B, C, and D. These enhanced lung sounds were obtained by applying the algorithm with different sets of parameter values, as shown in Table II. In order to increase robustness of result findings, the experiment was divided into two groups consisting of eight and nine listeners, respectively. Each group was presented with a different set of lung sound excerpts, making sure that at least one excerpt from all 22 distinct patients were contained within each set. In order to minimize selection bias, fatigue, and concentration effects, the sound excerpts were presented in randomized order for every participant. The list of presented choices was also randomized so that, on the test screen, choice A would not necessarily correspond to algorithmic version A for different sound excerpts, and similarly for choices B, C, and D.

Listeners were given a detailed instruction sheet and presented with one sound segment at a time. They were asked to listen to each original sound and the enhanced versions as many times as needed. Listeners indicated their preferred choice while considering the preservation or enhancement of lung sound content and breaths, and the perceived sound quality. Instructions clearly stated that this was a subjective listening task with no correct answer. If participants preferred more than one options, they were instructed to just choose one of them. If they preferred all of the enhanced versions the same, but better than the original, an extra choice, "Any," (brief for "Any of A, B, C, D") was added.

TABLE II

Implementation Details Behind Algorithms A, B, C, and D Running on Different Short-Time Analysis Windows, Frequency Band Splitting and Selection of the Band-Subtraction Factor $\delta_k$

|  | A | B | C | D |
|---|---|---|---|---|
| Window (ms) | 50 | 50 | 50 | 80 |
| Band Split | log | equilinear | log | log |
| Selection $\delta_k$ | $\delta_k^{(1)}$ | $\delta_k^{(1)}$ | $\delta_k^{(2)}$ | $\delta_k^{(1)}$ |

C. Dataset

Data included in the listening experiment was chosen "pseudo-randomly" from the entire dataset available. Although initial 3 s segments were chosen randomly from the entire data pool, the final dataset was slightly augmented in order to include: 1) abnormal occurrences comprising of wheeze, crackles or other; 2) healthy breaths; and 3) abnormal and normal breaths in both low- and high-noise environments. A final selection step ensured that recordings from different body locations were among the tested files.

Figure 16:
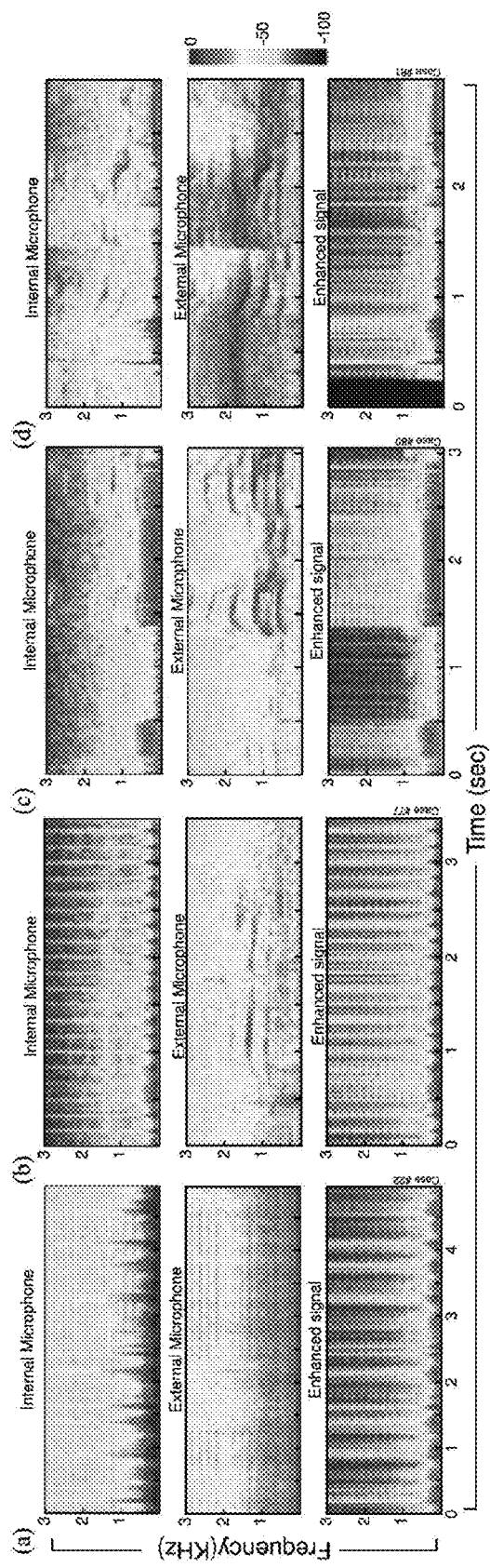
FIG. 16 shows spectrogram representations of four lung sound excerpts, including representations based on an internal microphone, representations based on the external microphone, and representations based on the signal as outputted by spectral subtraction algorithm according to an embodiment.

FIG. 16 shows spectrogram representations of four lung sound excerpts. The top panel of each column shows a representation based on the internal microphone. The middle panel shows a representation based on the external microphone recording. The bottom panel shows a representation based on the signal as outputted by spectral subtraction algorithm B. The quasi-periodic energy patterns, more pronounced in (a) and (b), correspond to the breathing and heart cycles and are well preserved in the enhanced signal. Column (a) shows removal of electronic interference contaminations and column (b) shows a soft background cry was successfully removed. Columns (c) and (d) show cases heavily contaminated by room noise and loud background crying, which have substantially been suppressed using the algorithm. Notice how concurring adventitious events were kept intact in (c) at 1.5-3 s and in (d) at 0.6-0.8 s. The period at the beginning of (d) corresponded to an interval of no contact with the child's body and was silenced after the post-processing algorithm.

V. Results

The validation of the enhancement algorithm of the current example requires a balance of the audio signal quality along with a faithful conservation of the spectral profile of the lung signal. It is also important to consider that clinical diagnosis using stethoscopes is ideally done by a physician or health care professional whose ear has been trained accordingly, i.e., for listening to stethoscope-outputted sounds. Any signal processing to improve quality should not result in undesired signal alterations that stray too far from the "typical" stethoscope signal, since the human ear will be interpreting the lung sounds at this time. For instance, some aspects of filtering result in "tunnel hearing" effects, which would be undesirable even if the quality is maintained. In order to properly assess the performance of the algorithm of this example, three forms of evaluations were used: visual inspection, objective signal analyses, and formal listening tests, as detailed below. The field recordings employed in the current study were also used to compare the performance of existing enhancement algorithms from the literature.

A. Visual Inspection

As discussed above, FIG. 16 shows the time-frequency profile of four lung sound excerpts (one excerpt per column). Typical energy components that emerge from such spectrograms are the breaths and heart beats, producing repetitive patterns that follow the child's respiratory and heart rate (see columns (a) and (b) of FIG. 16). Such energy components are well preserved in the enhanced signals (bottom). Middle rows depict concurrent noise distortions captured by the external microphone. Contamination examples include mobile interference (column (a)) and background chatting or crying (columns (b)-(d)), which have successfully been suppressed or eliminated, providing a clearer image of the lung sound energies.

B. Objective Validation of Processed Signals

To further assess improvements on the processed signals, objective methods were used to compare the signals before and after processing. Choosing an evaluation metric for enhancement is a nontrivial issue; many performance or quality measures commonly proposed in the literature often require knowledge of the true clean signal or some estimate of its statistics. This is not feasible in the current application: biosignals, such as lung sounds, have both general characteristics that can be estimated over a population, but also carry individual traits of each patient that should be carefully estimated. It is also important to maintain the adventitious events in the lung sound while mitigating noise contamination and other distortions. To provide an objective assessment of the system and method of this embodiment, a number of qualitative and quantitative measures were employed that come from telecommunication and speech processing fields but that were uniquely designed to the problem at hand. The metrics were chosen to assess how much shared information remains in the original and enhanced signals, relative to the background noise recording. While it is important to stress that these are not proper measures of signal quality improvement, they provide an informative assessment of shared signal characteristics before and after processing.

1) Segmental Signal-to-Noise Ratio (fSNRseg): Objective quality measure estimated over short-time windows accounting for signal dynamics and non-stationarity of noise [13]

$$fSNRseg = \frac{10}{T}\sum_{t=1}^{T} \frac{\sum_{k=1}^{K} w_k SNR^F}{\sum_{k=1}^{K} w_k} \tag{7}$$

with $SNR^F = \log_{10}\{(|X(k,\tau)|^2)/(|X(k,\tau)|-|\hat{X}(k,\tau)|)^2\}$, where $w_k$ represents the weight for frequency band k, $\hat{X}$ represents the processed signal, and X typically represents the clean (desired) signal. As mentioned above, in this paper, X will represent the background noise, since the clean uncontaminated signal in not available. $SNR^F$ is calculated over short-time windows of 30 ms to account for signal dynamics and nonstationarity of noise using a Hanning window. For each frame, the spectral representations $X(k,\tau)$ and $\hat{X}(k,\tau)$ are computed by critical band filtering. The bandwidth and center frequencies of the 25 filters used and the perceptual (Articulation Index) weights $w_k$ follow the ones proposed in [24] and [14]. Using the described method, fSNRseg value can reach a maximum of 35 when the signals under comparison are identical. Comparatively, a minimum value just below −8 can be achieved when one of the signals comes from a white Gaussian process.

2) Normalized-Covariance Measure (NCM): A metric used specifically for estimated speech intelligibility (SI) by accounting for audibility of the signal at various frequency bands. It is a speech-based speech transmission index measure capturing a weighted average of a signal to noise quantity $SNR^N$, where the latter is calculated from the covariance of the envelopes of the two signals over different frequency bands k [25] and normalized to [0,1]. The band-importance weights $w_k$ followed ANSI-1997 standards [26]. Though this metric is speech-centric (as many quality measures in the literature), it is constructed to account for audibility characteristics of the human ear, hence reflecting a general account of improved quality of a signal as perceived by a human listener:

$$NCM = \left\{\sum_{k=1}^{K} w_k SNR^N(k)\right\} / \sum_{k=1}^{K} w_k. \quad (8)$$

3) Three-Level Coherence Speech Intelligibility Index (CSII): The CSII metric is also a SI-based metric based on the ANSI standard for the speech intelligibility index (SII). Unlike NCM, CSII uses an estimate of SNR in the spectral domain, for each frame $\tau=1, \ldots, T$: the signal-to-residual $SNR_{ESI}^N$; the latter is calculated using the roex filters and the magnitude-squared coherence followed by [0, 1] normalization. A 30-ms Hanning window was used and the three-level CSII approach divided the signal into low-, mid-, and high-amplitude regions, using each frame's root-mean-square level information [13], [27]

$$CSII = \frac{1}{T}\sum_{\tau=1}^{T} \frac{\sum_{k=1}^{K} w_k SNR_{ESI}^N(k, \tau)}{\sum_{k=1}^{K} w_k}. \quad (9)$$

All metrics generally require knowledge of the ground truth undistorted lung signal, which is not available in the setup of this example. However, they are contrasted to show how much information is shared between the improved and the background(noise) signal, relative to the non-processed (original) auscultation signal. Specifically, each metric was computed between the time waveforms of the original y(n) and the background noise d(n) signals, then contrasted for the enhanced $\hat{x}(n)$ and the background $\hat{d}(n)$ signals. The higher the achieved metric value, the "closer" the compared signals are, with respect to their sound contents.

Figure 17:
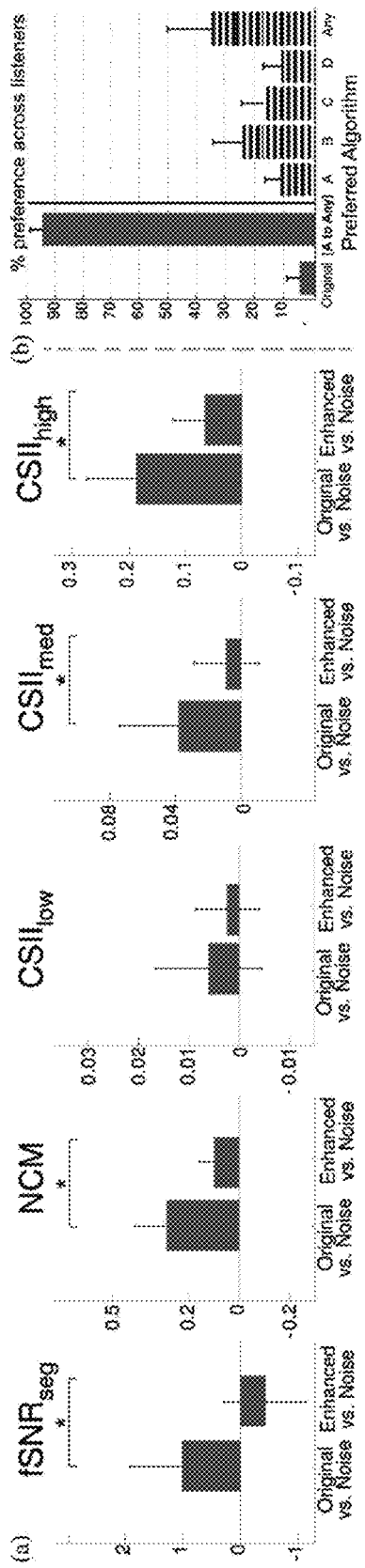
FIG. 17 shows results of a listening evaluation performed on samples processed according to an embodiment.

FIG. 17 shows results of the evaluations. The average results with error bars on the evaluation of objective, quality, and intelligibility measures for original noisy signal (left bar) and the enhanced signal (right bar), compared with noise as the ground truth, are shown in the five segments of section (a) of FIG. 17. Enhanced signals were found to be more "distant" representations of the noise signals. Stars indicate statistically significant differences. The final segment in section (b) of FIG. 17 shows average responses of the listening test where bars indicate the preference percentage per choice. On the left, the solid bars show overall results, comparing average preference of the original sounds versus preference of any of the enhanced versions. The bar labeled [A to Any] includes choices {A, B, C, D, Any}. On the right, the dashed bars show the breakdown among all choices. Choice Any of A, B, C, D has been abbreviated to Any.

As discussed above, FIG. 17(a) shows histogram distribution results for each metric: fSNRseg yielded, on average, a value of 1.02 between the original and the noise signals, likely reflecting leak through the surrounding environment to the internal microphone. Such measure was reduced to −0.44 when contrasting the improved with the noise signal indicating reduced joint information. The two distributions were statistically significantly different (paired t-test: t-statistic=15.99 and p-value $p_t$=3E—13; Wilcoxon: Z-statistic=4.5 and p-value $p_w$=8E−6) providing evidence that the original signal was "closer"—statistically—to the surrounding noise, relative to the enhanced signal. Significant difference was also observed in all other metrics [see FIG. 17(a)] with NCM ($p_t$=1E−10; $p_w$=2E−6), $CSII_{med}$ ($p_t$=1E−10; $p_w$=3E−5), and $CSII_{high}$ ($p_t$=7E−10; $p_w$=7E−6).

C. Listening Experiment

While objective signal metrics hint to significant improvements in the original recording post-processing, the way to effectively validate the denoising value of the proposed algorithm along with its clinical value for a health care professional is via perceptual listening tests by a panel of experts. Following the methods described in Section IV, the perceived quality of the processed signals was assessed with formal listening evaluations.

Segment (b) of FIG. 17 summarizes the opinions of the panel of experts. Considering all listeners and all tested sound excerpts, the bars indicate the percentage of preference among the available choices. Bar plots were produced by first forming a contingency table per listener, counting his/her choice preferences, and then averaging across listeners. The vertical lines depict the standard variation among all listeners. The listed choices on the x-axis correspond one by one to the ones presented during the listening test, where choice "Any of A, B, C, D" has been abbreviated to "Any." An extra panel "[A to Any]" is added here illustrating preference percentages for any enhancement version of the algorithm, irrespective of choice of parameters. On average, listeners prefer mostly choice "Any" (34.06% of the time), followed by choices "B" and "C." Overall, listeners prefer the enhanced signal relative to the original unprocessed signal 95.08% of the time. Considering responses across groups of listeners, results are consistent across Group 1 and Group 2. A statistical analysis across the two groups using a parametric t-test and a nonparametric Wilcoxon rank sum test shows no difference among the two populations except possibly for choice D. The corresponding pvalues for the t-test and the Wilcoxon test ($p_t$, $p_w$) are: for choice "Original": (0.28, 0.23); choice "A": (0.37, 0.52); choice "B": (0.74, 0.62); choice "C":(0.33, 0.74); choice "D":(0.08, 0.10); choice "Any": (0.11, 0.05); and choice "[A to Any]": (0.28, 0.23).

Analyzing the results, choice "C" is preferred over "B" when the test sound consists of a low or fade normal breath. To better understand this preference, it is important to note that algorithm C is relaxed for higher frequencies due to the $\delta_k$ parameter. Qualitatively, all low-breath excerpts retained the normal breath information after noise suppression, but with an added softwind sound effect. This wind distortion or hissing was at a lower frequency range for algorithm B and proved to be less pleasant than the one produced by algorithm C, which ranged in higher frequencies. This observation was consistent across different files and listeners. Looking further into algorithm C, a larger preference variation was noticed for Group 2 when compared to Group 1. This variation was found to be produced by two participants who preferred "C" over any other choice 35% of the time and both preferred the original only in two cases.

The original recording was preferred 4.9% of the time. While this percentage constitutes a minority on the tested cases, a detailed breakdown provides valuable insights on the operation of the enhancement algorithm. In most cases, it is determined that low-volume resulting periods affect the listeners' judgments.

Clipping distortions make abnormal sound events even more prominent. Clipping tends to corrupt the signal content and produce false abnormal sounds for loud breaths. However, when such clipping occurs during crackle events, it results in more distinct abnormal sounds, which can be better perceived than a processed signal with muted clipping. For two such sound files in Group 1, 2/8 users prefer the original raw audio and for one such file in Group 2, 2/9 prefer the original.

Child vocalization are typically removed after enhancement. Since the algorithm operates with the internal recording as a metric, any sound captured weakly by the internal but strongly by the external microphone is flagged as noise. One such file in Group 2 leads 4/9 users to prefer the original sound: a faint child vocalization is highly suppressed in the enhanced signal. As users are not presented with the external recording information, it can be hard to tell the origin of some abnormal sounds that overlap with profiles of abnormal breaths. Nevertheless, a post-analysis on the external microphone shows that this is indeed a clear child vocalization.

Reduced normal breath sounds. The algorithm has an explicit subtractive nature; the recovered signal is, thus, expected to have lower average energy compared to the original internal recording. Before the listening test, all recordings are amplified to the same level; however, isolated time periods of the enhanced signal are still expected to have lower amplitude values than the corresponding original segment, especially for noisy backgrounds. This normalization imbalance has perceivable effects in some test files. For auscultation recordings in lower site positions, breath sounds can be faintly heard, and the subtraction process reduces those sounds even further. Two such cases were included in the listening test, where suppression of a loud power generator noise resulted in a faded post-processed breath sound. In this case, listeners preferred the original file where the breath sounds stronger than the processed version.

A finalized enhancement algorithm may consist of parametric choices that combine versions B and C. The smoother subtraction scheme enforced by factor $\delta(2)k$ is kept along with the equilinear model of frequency band splitting using a 50-ms frame size window. An informal validation by a few members of the original expert panel confirms that the combined algorithm parameters result in improved lung sound quality and preservation of low breaths.

D. Comparison of Results

As discussed above, existing methods typically consider auscultations in soundproof chambers, highly controlled environments with low ambient or Gaussian noise. Moreover, the term noise often refers to suppressing heart sounds in the context of healthy lung sound analysis, or to separate normal airflow from abnormal explosive occurrences. Extending results from previous systems and methods to realistic settings is nontrivial, particularly in nonhealthy patients where abnormal lung events occur in an unpredictable manner and whose signal characteristics may overlap with those of environmental noise.

The results of the embodiment of the current example can be contrasted with the performance of other lung sound enhancement schemes, which mainly focus on the postclassification of auscultation sounds, rather than the production of improved-quality auscultation signals to be used by health care professionals in lieu of the original recording. One such technique is the speech-based spectral subtractive scheme of Boll [35], which has well documented shortcomings. As another comparison, a more robust instantiation of speech-based spectral subtraction is used, which we call here speechSP. The system and method of the current example were compared with speechSP, maintaining the same window size, window overlap factor, and number of frequency bands of Section III-B; both algorithms were applied on the same preprocessed signals after downsampling, normalizing, and correcting for clipping distortions.

Figure 18:
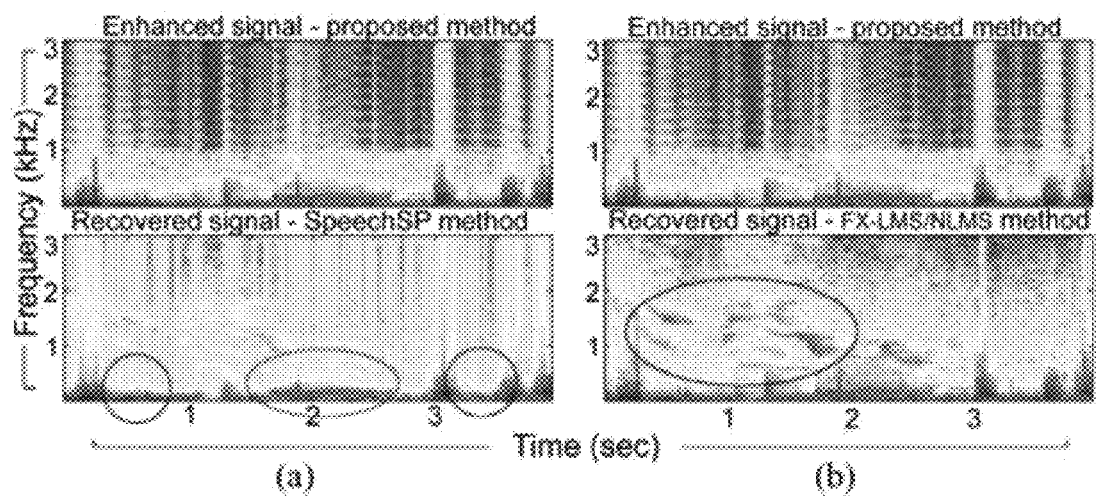
FIG. 18 shows spectrogram representations comparing results of an embodiment with other processing techniques.

FIG. 18 shows spectrogram illustrations comparing the method of the embodiment of this example with (a) speechSP and (b) FX-LMS applied on the same sound excerpt. SpeechSP suppresses important lung sounds like crackle patterns (black circles in section (b) and on the left and right sides of section (a) of FIG. 18) and wheeze pattern (blue, elongated circle in section (a) of FIG. 18). FX-LMS convergence is challenged by both the parametric setup and the complex, abrupt noise environment resulting in nonoptimal lung sound recovery. The colormap of FIG. 18 is the same as in FIG. 16.

A visual inspection of the speechSP method is sufficient to observe the notable resulting artifacts. FIG. 18, section (a) illustrates an example comparing the two methods when applied on the same auscultation excerpt. SpeechSP algorithm highly suppressed the wheezing segment around 2 s in FIG. 18, section (a), along with the crackle occurrences around 0.5 and 3.5 s. In the example shown, the speechSP method suffered from significant sound deterioration; and in the majority of cases, the speechSP-processed signal was corrupted by artifacts impeding the acoustic recognition of alarming adventitious events. Overall, the combination of visual inspection, signal analysis and informal listening tests, clearly indicates that speechSP maximizes the subtraction of background noise interference, at the expense of deterioration of the original lung signal as well as significant masking of adventitious lung events. Both effects are largely caused by its speech-centric view which considers specific statistical and signal characteristics for the fidelity of speech that do not match the nature of lung signals.

Next, the method of the current example was compared to active noise cancellation (ANC) schemes. Such algorithms typically focus on noise reduction using knowledge of a primary signal and at least one reference signal. In the present example, the case of a single reference sensor and use a feed-forward Filtered-X Least Mean Squared algorithm (FX-LMS) is considered. FX-LMS has been previously used for denoising in auscultation signals recorded in a controlled acoustic chamber with simulated high-noise interference. An implementation of the normalized LMS (NLMS) is adopted in this example. Using all signals of the study, the effectiveness of the NLMS in suppressing external noise interference was tested. The filter coefficients were optimized in the MSE sense with filter tap-order NLMS varying between [4, . . . , 120], step size ηLMS varying between [1E-8, . . . , 2] and denominator term offset step size CLMS in [1E-8, . . . , 1E-2]. A representative example is shown in FIG. 18, section (b); zero initial filter weights were assumed with the optimal solution occurring for (NLMS, ηLMS, CLMS)=(90, 5E-7, 1E-8). The results indicate that NLMS fails to sufficiently reduce the effect of external noise, especially in low SNR instances or during abrupt transitions in background interferences.

It is known that difficult acoustic environments typically pose a challenge to ANC methods for auscultation where ambient recordings are rendered ineffective as reference signals. This limitation is due to a number of reasons. First, the presence of uncorrelated noise between the primary and reference channels largely affects the convergence of NLMS and the performance of the denoising filter. Nelson et al. have indeed demonstrated that using an external microphone is suboptimal in case of auscultation recordings, proposing use of accelerometer-based reference mounted on the stethoscope in line with the transducer, a nonfeasible setup for the application of the current example. Furthermore, iterative filter updates in the NLMS are heavily dependent on the statistics of the observed signal and reference noise. Abrupt changes in signal statistics pose real challenges in updating filter parameters fast enough to prevent divergence. This is particularly true in field auscultation recordings where brusque changes in the signal often occur due to poor body seal of the stethoscope—caused by child movement or change of auscultation site. Noise sources are also abruptly appearing and disappearing from the environment (e.g., sudden patient cry, phone ring); hence, posing additional challenges to the convergence of the algorithm without any prior constraints or knowledge about signal statistics or anticipated dynamics. Furthermore, unfavorable initial conditions of the algorithm can highly affect the recovered signal and lead to intractable solutions.

VI. Discussion

In this example, the task of suppressing noise contaminations from lung sound recordings is addressed by proposing an adaptive subtraction scheme that operates in the spectral domain. The algorithm processes each frequency band in a nonuniform manner and uses prior knowledge of the signal of interest to adjust a penalty across the frequency spectrum. It operates in short-time windows and uses the current frame's signal-to-noise information to dynamically relax or strengthen the noise suppression operation. As is the case with most spectral subtraction schemes, the current algorithm is formulated for additive noise and is unable to handle convolutive or nonlinear effects. A prominent example of such distortions are clipping effects which are processed separately in this paper and integrated with the proposed algorithm.

The efficiency and success of the proposed algorithm in suppressing environmental noise, while preserving the lung sound content, was validated by a formal listening test performed by a panel of expert physicians. A set of abnormal and normal lung sounds were used for validation, chosen to span the expected variability in auscultation signals, including the unexpected presence of adventitious lung events and low breath sounds. The expert panel judgments reveal a strong preference for the enhanced signal. Post hoc analysis and informal followup listening tests suggest that simple volume increase can help to balance few cases where the desired lung sound is perceived as weak.

In previous work on lung sound processing with the aid of computerized analysis, work has been done on airflow estimation, feature extraction, and detection of abnormal sounds and classification, while recordings were acquired in quiet or soundproof rooms to overpass the inherent difficulty of noisy environments. In this context, noise cancellation typically refers to heart sound suppression and a wide range of techniques have successfully been used: high-pass filtering, adaptive filtering, higher-order statistics, independent component analysis, or multiresolution analysis. On the other hand, very few studies address ambient noise in lung sound recordings and results are typically presented on a small number of sounds, using graphical methods or informal listening. The study of this example focused on real-environment noise cancellation, applicable to both normal and abnormal respiratory sounds, and evaluated on a large scale by objective/quality measures and a panel of expert physicians.

The strengths and benefits of the proposed embodiment lie in the simple automated setup and its adaptive nature; both are fundamental conditions for applicability in everyday clinical environments, especially in crowded low-resource health centers, where the majority of childhood respiratory morbidity and mortality takes place. By design, the proposed approach can be simply extended to a real-time implementation and integrated with lung sound acquisition protocols. By improving the quality of auscultation signals picked-up by stethoscopes, the study hopes to provide medical practitioners with an improved recording of lung signals that minimizes the effect of environmental distortions and improves and facilitates the interface between auscultation and automated methods for computerized analysis and recognition of auscultation signals.

Example 2

The specific parameters used in the above example represent only some embodiments of the current invention. Parameters can be adjusted as needed for the task at hand. There may be a range of acceptable parameters for certain uses, which may include optimal ranges or values. The following provides examples of some ranges suitable for some embodiments.

The full frequency range of 0-4 kHz can be split into different numbers of bands according to various embodiments. In speech applications, 4 to 8 bands are typically used. In testing of an example embodiment, the lower end of preferred range was 6 bands, where fewer than 6 bands was deemed too small for the some applications and produced wide frequency bands. 32 bands was found to be optimal in some cases, and showed better target enhancement, especially in very noisy environments containing crying. It is possible to use even more bands. In one example, 64 bands were used and were shown to be adequate. However, increasing the number of bands can introduce a large number of extra parameters for the model. In some embodiments, 64 bands may be considered an upper bound of the optimal ranges.

There are different modes of frequency splitting, including linear, equal-energy linear (equi-linear), logarithmically, and mel-frequency scale. These methods have comparable effects. Equi-linear may be preferable or optimal when the environment is very noisy and it can result in a more pleasant sound to the listener's ear than other choices. Very minor effects on signal quality may be observed with other modes of frequency splitting.

The time window of short-time processing may also be adjusted according to some embodiments. In examples of one embodiment, a window of approximately 50 msec was optimal. A window of <20 msec produced unpleasant distortions in the form of high frequency hissing. A window of >100 msec produced low frequency noise, which mostly affected those sounds events that indicate lung disease, corrupting those sounds to be very different than what physicians are used to hearing.

REFERENCES

1. X. Lu and M. Bahoura, "An integrated automated system for crackles extraction and classification," Biomed. Signal Process. Control, vol. 3, no. 3, pp. 244-254, July 2008.
2. R. J. Riella et al., "Method for automatic detection of wheezing in lung sounds," Brazilian J. Med. Biol. Res., vol. 42, no. 7, pp. 674-684, July 2009.
3. D. Emmanouilidou et al., "A multiresolution analysis for detection of abnormal lung sounds," in Proc. IEEE Annu. Int. Conf. Eng. Med. Biol. Soc., 2012, pp. 3139-3142.
4. K. K. Guntupalli et al., "Validation of automatic wheeze detection in patients with obstructed airways and in healthy subjects," J. Asthma, Off. J. Assoc. Care Asthma, vol. 45, no. 10, pp. 903-907, December 2008.
5. L. E. Ellington et al., "Developing a reference of normal lung sounds in healthy peruvian children," Lung, vol. 192, pp. 765-773, Jun. 19, 2014.
6. N. Gavriely et al., "Spectral characteristics of chest wall breath sounds in normal subjects," Thorax, vol. 50, no. 12, pp. 1292-1300, December 1995.
7. S. K. Chowdhury and a. K. Majumder, "Frequency analysis of adventitious lung sounds." Journal of biomedical engineering, vol. 4, no. 4, pp. 305-12, October 1982. [Online]. Available: http://www.ncbi.nlm.nih.gov/pubmed/7144154.
8. N. Meslier et al., "Wheezes," Eur. Respir. J., vol. 8, no. 11, pp. 1942-1948, November 1995.
9. P. Piirila and A. Sovijarvi, "Crackles: Recording, analysis and clinical significance," Eur. Respir. J., vol. 8, no. 12, pp. 2139-2148, December 1995.
10. B. Flietstra et al., "Automated analysis of crackles in patients with interstitial pulmonary fibrosis," Pulmonary Med., vol. 2011, no. 2, pp. 5905-5906, 2011.
11. H. Pasterkamp et al., "Nomenclature used by health care professionals to describe breath sounds in asthma," Chest, vol. 92, no. 2, pp. 346-352, August 1987.
12. K. K. Guntupalli et al., "Validation of automatic wheeze detection in patients with obstructed airways and in healthy subjects," J. Asthma, Off. J. Assoc. Care Asthma, vol. 45, no. 10, pp. 903-907, December 2008.
13. G. Prasad, "A review of different approaches of spectral subtraction algorithms for speech enhancement," Curr. Res. Eng., vol. 1, no. 2, pp. 57-64, 2013.
14. P. C. Loizou, Speech Enhancement: Theory and Practice, 2nd ed. Boca Raton, Fla., USA: CRC Press, 2013.
15. P. Vary, "Noise suppression by spectral magnitude estimation-mechanism and theoretical limits," Signal Process., vol. 8, pp. 387-400, 1985.
16. D. Emmanouilidou and M. Elhilali, "Characterization of noise contaminations in lung sound recordings," in Proc. IEEE 35th Annu. Int. Conf. Eng. Med. Biol. Soc., 2013, pp. 2551-2554.
17. A. R. A. Sovijarvi et al., "Standardization of computerized respiratory sound analysis," Eur. Respir. Rev., vol. 10, no. 77, p. 585, 2000.
18. J. Beh and H. Ko, "Spectral subtraction using spectral harmonics for robust speech recognition in car environments," in Proc. Int. Conf. Comput. Sci., 2003, pp. 1109-1116.
19. (1999). The PERCH (Pneumonia Etiology Research for Child Health) Project. [Online]. Available: www.jhsph.edu/research/centersand-institutes/ivac/projects/perch/
20. World Health Organization. (2006, July). Pocket book of hospital care for children: Guidelines for the management of common illnesses with limited resources. [Online]. Available: http://www.who.int/maternal_child_adolescent/documents/9241546700/en/.
21. L. L. Schumaker, Spline Functions: Basic Theory. New York, N.Y., USA: Wiley, 1981.
22. S. Reichert et al., "Analysis of respiratory sounds: State of the art," Clin. Med. Circulatory Respir. Pulmonary Med., vol. 2, pp. 45-58, 2008.
23. A. Gurung et al., "Computerized lung sound analysis as diagnostic aid for the detection of abnormal lung sounds: A systematic review and meta-analysis," Respir. Med, vol. 105, no. 9, pp. 1396-1403, September 2011.
24. P. T. C. A. Quackenbush and R. Schuyler Barnwell, Objective Measures of Speech Quality, 1st ed. Englewood Cliffs, N.J., USA: Prentice-Hall, 1998.
25. J. Ma et al., "Objective measures for predicting speech intelligibility in noisy conditions based on new band-importance functions," J. Acoust. Soc. Amer., vol. 125, no. 5, pp. 3387-3405, May 2009.
26. Methods for Calculation of the Speech Intelligibility Index, ANSI-S3.5-1997-R2007, 1997.
27. J. M. Kates and K. H. Arehart, "Coherence and the speech intelligibility index," J. Acoust. Soc. Amer., vol. 117, no. 4, pp. 2224-2237, 2005.
28. N. Al-Naggar, "A new method of lung sounds filtering using modulated least mean squareadaptive noise cancellation," J. Biomed. Sci. Eng., vol. 2013, pp. 869-876, September 2013.
29. M. Molaie et al., "A chaotic viewpoint on noise reduction from respiratory sounds," Biomed. Signal Proc. Control, vol. 10, pp. 245-249, 2014.
30. I. Hossain and Z. Moussavi, "An overview of heart-noise reduction of lung sound using wavelet transform based filter," in Proc. IEEE 25th Annu. Int. Conf. Eng. Med. Biol. Soc., 2003, vol. 1, pp. 458-461.
31. F. Ghaderi et al., "Localizing heart sounds in respiratory signals using singular spectrum analysis," Biomed. Eng., vol. 58, no. 12, pp. 3360-3367, December 2011.
32. L. J. Hadjileontiadis, Lung Sounds: An Advanced Signal Processing Perspective. San Rafael, Calif., USA: Morgan & Claypool, 2009, vol. 3, no. 1.
33. M. Bahoura et al., "Respiratory sounds denoising using wavelet packets," in Proc. 2nd Int. Conf. Bioelectromagn., 1998, pp. 11-12
34. G.-C. Chang and Y.-F. Lai, "Performance evaluation and enhancement of lung sound recognition system in two real noisy environments," Comput. Methods Progr. Biomed, vol. 97, no. 2, pp. 141-150, 2010.
35. S. Boll, "Suppression of acoustic noise in speech using spectral subtraction," IEEE Trans. Acoust, Speech, Signal Process., vol. ASSP-27, no. 2, pp. 113-120, April 1979.
36. M. Berouti et al., "Enhancement of speech corrupted by acoustic noise," in Proc. IEEE Int. Conf. Acoust., Speech, Signal Process., April 1979, vol. 4, pp. 208-211.
37. P. Lockwood and J. Boudy, "Experiments with a nonlinear spectral subtractor (NSS), hidden Markov models and the projection, for robust speech recognition in cars,"

Speech Commun., vol. 11, nos. 2/3, pp. 215-228, 1992.10 IEEE TRANSACTIONS ON BIOMEDICAL ENGINEERING, VOL. 00, NO. 0, 2015.
38. L. Singh and S. Sridharan, "Speech enhancement using critical band spectral subtraction," in Proc. Int. Conf. Spoken Lang. Proc. Sydney, Australia, 1979, pp. 2827-2830.
39. S. B. Patel et al., "An adaptive noise reduction stethoscope for auscultation in high noise environments," J. Acoust. Soc. Amer., vol. 103, no. 5, pp. 2483-2491, May 1998.
40. G. Nelson et al., "Noise control challenges for auscultation on medical evacuation helicopters," Appl. Acoust., vol. 80, pp. 68-78, 2014.
41. S. M. Kuo and D. R. Morgan, "Active noise control: A tutorial review," Proc. IEEE, vol. 87, no. 6, pp. 943-973, June 1999.
42. S. Haykin, Adaptive Filter Theory (3rd Ed.). Upper Saddle River, N.J., USA: Prentice-Hall, Inc, 1996.
43. J. M. Valin and I. B. Collings, "Interference-normalized least mean square algorithm," IEEE Signal Proc. Lett., vol. 14, no. 12, pp. 988-991, December 2007.
44. E. V. Kuhn et al., "Stochastic modeling of the NLMS algorithm for complex gaussian input data and nonstationary environment," Digital Signal Process., vol. 30, pp. 55-66, 2014.
45. L. J. Hadjileontiadis, "A novel technique for denoising explosive lung sounds emnpirmical mode decompiosition and fractal dimension foilter," IEEE Eng. Med. Biol. Mag., vol. 26, no. 1, pp. 30-39, January 2007.
46. A. Suzuki et al., "Real-time adaptive cancelling of ambient noise in lung sound measurement," Med. Biol. Eng. Comput., vol. 33, no. 5, pp. 704-708, September 1995.

We claim:

1. An electronic stethoscope comprising:
    an acoustic sensor assembly having a first microphone arranged to detect biological sounds within a body under observation;
    a detection system in communication with said first microphone and configured to receive an auscultation signal from said first microphone, said auscultation signal comprising information of said biological sounds detected by said first microphone; and
    a second microphone arranged to detect noise from an environment of said body, said second microphone being in communication with said detection system, which is configured to receive a noise signal from said second microphone, wherein said auscultation signal and said noise signal are detected substantially simultaneously and in-phase,
    wherein said detection system is configured to provide a resultant signal based on said auscultation signal and said noise signal, said resultant signal comprising the information of said biological sounds, and
    wherein said detection system is configured to subtract an adjusted noise signal from said auscultation signal to produce said resultant signal, wherein said adjusted noise signal is calculated based on said noise signal adjusted by a plurality of spectral weighting factors across a plurality of time windows and a plurality of frequency bands, wherein each of said spectral weighting factors is individually selected at each frequency band to block predetermined higher frequency ranges of said noise signal compared to a lower frequency range corresponding to said biological sounds,
    wherein the plurality of spectral weighting factors comprise a signal-to-noise ratio (SNR) weighting factor for each of the plurality of frequency bands and a spectral weighting factor in a frequency domain across the plurality of frequency bands selected to enhance the auscultation signal at one or more first frequency bands in the plurality of frequency bands and penalize the auscultation signal at one or more second frequency bands different from the one or more first frequency bands in the plurality of frequency bands depending on a spectral profile of the noise signal.

2. An electronic stethoscope according to claim 1, wherein said detection system is further configured to add a portion of said noise signal to said resultant signal using a weighing factor.

3. An electronic stethoscope according to claim 2, wherein an amount of said portion of said noise signal that is added is based on a signal to noise ratio of said auscultation signal.

4. An electronic stethoscope according to claim 1, wherein each of said spectral weighting factors is uniquely associated with one of said frequency bands, and wherein values of said spectral weighting factors increase with the increase of values of said frequency bands.

5. An electronic stethoscope according to claim 1, wherein said noise signal is further adjusted by a plurality of frequency-dependent oversubtraction factors across the plurality of time windows and the plurality of frequency bands, wherein each of said frequency-dependent oversubtraction factors is calculated based on a signal to noise ratio of said auscultation signal for a selected time window such that values of said frequency-dependent oversubtraction factors increase with a decrease of values of said signal to noise ratio of said auscultation signal across the plurality of time windows.

6. An electronic stethoscope according to claim 1, wherein at least a portion of said auscultation signal for adjacent time windows is smoothed at each of said frequency bands.

7. An electronic stethoscope according to claim 1, wherein said detection system is further configured to identify at least one of a physical process of said body and a physiological condition of said body based on at least one of a temporal characteristic and a spectral characteristic of said resultant signal.

8. A method of processing signals detected by an electronic stethoscope, the method comprising:
    obtaining an auscultation signal from a body under observation with said electronic stethoscope, said auscultation signal comprising a target body sound;
    obtaining a noise signal comprising noise from an environment of said body, wherein said auscultation signal and said noise signal are detected substantially simultaneously and in-phase; and
    obtaining a resultant signal by subtracting adjusted noise from said auscultation signal, said resultant signal comprising said target body sound,
    wherein said adjusted noise signal is calculated based on at least a portion of said noise signal adjusted by a plurality of spectral weighting factors across a plurality of time windows and a plurality of frequency bands, wherein each of said spectral weighting factors is individually selected at each frequency band to block predetermined higher frequency ranges of said noise signal compared to a lower frequency range corresponding to said target body sound, wherein the plurality of spectral weighting factors comprise a signal-to-noise ratio (SNR) weighting factor for each of the plurality of frequency bands and a spectral weighting factor in a frequency domain across the plurality of frequency bands selected to enhance the auscultation signal at one or more first frequency bands in the plurality of frequency bands and penalize the auscultation signal at one or more second frequency bands different from the one or more first frequency bands in the plurality of frequency bands depending on a spectral profile of the noise signal.

9. A method of processing signals according to claim 8, the method further comprising:
adding a portion of said noise signal to said resultant signal using a weighing factor.

10. An electronic stethoscope according to claim 9, wherein an amount of said portion of said noise signal that is added is based on a signal to noise ratio of said auscultation signal.

11. A method of processing signals according to claim 8, wherein each of said spectral weighting factors is uniquely associated with one of said frequency bands, and wherein values of said spectral weighting factors increase with the increase of values of said frequency bands.

12. A method of processing signals according to claim 8, wherein said noise signal is further adjusted by a plurality of frequency-dependent oversubtraction factors across the plurality of time windows and the plurality of frequency bands, wherein each of said frequency-dependent oversubtraction factors is calculated based on a signal to noise ratio of said auscultation signal for a selected time window such that values of said frequency-dependent oversubtraction factors increase with a decrease of values of said signal to noise ratio of said auscultation signal across the plurality of time windows.

13. A method of processing signals according to claim 8, wherein at least a portion of said auscultation signal for adjacent time windows is smoothed at each of said frequency bands.

14. A method of processing signals according to claim 8, the method further comprising:
identifying at least one of a physical process of said body and a physiological condition of said body based on at least one of a temporal characteristic and a spectral characteristic of said resultant signal.

15. A non-transitory computer-readable medium comprising software, which when executed by a computer causes the computer to:
receive a first signal from an electronic stethoscope monitoring a body, said first signal comprising a target body sound;
receive a second signal comprising noise, wherein said first signal and said second signal are detected substantially simultaneously and in-phase; and
obtain a resultant signal by subtracting adjusted second signal from said first signal, said resultant signal comprising the target body sound,
wherein said adjusted second signal is calculated based on at least a portion of said second signal adjusted by a plurality of spectral weighting factors across a plurality of time windows and a plurality of frequency bands, wherein each of said spectral weighting factors is individually selected at each frequency band to block predetermined higher frequency ranges of said second signal compared to a lower frequency range corresponding to said target body sound,
wherein the plurality of spectral weighting factors comprise a signal-to-noise ratio (SNR) weighting factor for each of the plurality of frequency bands and a spectral weighting factor in a frequency domain across the plurality of frequency bands selected to enhance the auscultation signal at one or more first frequency bands in the plurality of frequency bands and penalize the auscultation signal at one or more second frequency bands different from the one or more first frequency bands in the plurality of frequency bands depending on a spectral profile of the noise signal.

16. A non-transitory computer-readable medium comprising software according to claim 15, which when executed further causes the computer to add a portion of said second signal to said resultant signal using a weighing factor.

17. A non-transitory computer-readable medium comprising software according to claim 16, wherein an amount of said portion of said noise signal that is added is based on a signal to noise ratio of said first signal.

18. A non-transitory computer-readable medium comprising software according to claim 15, wherein each of said spectral weighting factors is uniquely associated with one of said frequency bands, and wherein values of said spectral weighting factors increase with an increase of values of said frequency bands.

19. A non-transitory computer-readable medium comprising software according to claim 15, wherein said second signal is further adjusted by a plurality of frequency-dependent oversubtraction factors across the plurality of time windows and the plurality of frequency bands, wherein each of said frequency-dependent oversubtraction factors is calculated based on a signal to noise ratio of said first signal for a selected time window such that values of said frequency-dependent oversubtraction factors increase with a decrease of values of said signal to noise ratio of said first signal across the plurality of time windows.

20. A non-transitory computer-readable medium comprising software according to claim 15, wherein at least a portion of said auscultation signal for adjacent time windows is smoothed at each of said frequency bands.

21. A non-transitory computer-readable medium comprising software according to claim 15, which when executed further causes the computer to identify at least one of a physical process of said body and a physiological condition of said body based on at least one of a temporal characteristic and a spectral characteristic of said resultant signal.

* * * * *